US011484283B2

(12) United States Patent
Shekhar et al.

(10) Patent No.: US 11,484,283 B2
(45) Date of Patent: Nov. 1, 2022

(54) APPARATUS AND METHOD FOR IDENTIFICATION OF WHEEZING IN AUSCULATED LUNG SOUNDS

(71) Applicant: CHILDREN'S NATIONAL MEDICAL CENTER, Washington, DC (US)

(72) Inventors: Raj Shekhar, Washington, DC (US); Sukryool Kang, Washington, DC (US); Stephen Teach, Washington, DC (US); Shilpa Patel, Washington, DC (US); Dinesh Pillai, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 555 days.

(21) Appl. No.: 16/466,253

(22) PCT Filed: Dec. 4, 2017

(86) PCT No.: PCT/US2017/064537
§ 371 (c)(1),
(2) Date: Jun. 3, 2019

(87) PCT Pub. No.: WO2018/102821
PCT Pub. Date: Jun. 7, 2018

(65) Prior Publication Data
US 2020/0060641 A1 Feb. 27, 2020

Related U.S. Application Data

(60) Provisional application No. 62/429,605, filed on Dec. 2, 2016.

(51) Int. Cl.
A61B 7/00 (2006.01)
G16H 50/30 (2018.01)
(Continued)

(52) U.S. Cl.
CPC .......... *A61B 7/003* (2013.01); *A61B 5/14542* (2013.01); *A61B 5/744* (2013.01);
(Continued)

(58) Field of Classification Search
CPC ......... A61B 7/003; A61B 7/04; A61B 5/0816; A61B 5/7264; A61B 7/02; A61B 5/684; G16H 50/20; G16H 50/30
See application file for complete search history.

(56) References Cited

U.S. PATENT DOCUMENTS

2004/0228494 A1   11/2004   Smith
2008/0114266 A1 *  5/2008   Shen ...................... A61B 7/003
                                                        600/586
(Continued)

OTHER PUBLICATIONS

International Search Report and Written opinion dated Mar. 1, 2018 in PCT/US2017/064537 filed Dec. 4, 2017.

*Primary Examiner* — Christian Jang
*Assistant Examiner* — Karen E Toth
(74) *Attorney, Agent, or Firm* — Oblon, McClelland, Maier & Neustadt, L.L.P.

(57) ABSTRACT

Described herein are a computer enhanced medical method and device for generating an asthmatic condition indication. The apparatus receives a lung signal from a stethoscope, the lung signal having been converted from an analog signal to a digital signal. Furthermore, circuitry included in the apparatus performs, inter alia, the following: displays a patient recording canvas corresponding to physical locations on a body of the patient, the canvas including an anterior patient orientation and a posterior patient orientation, generates a recording process, the recording process including recording, for a predetermined period of time, the detected lung signal, and associates the recording with a marked location. Furthermore, the circuitry merges the recorded lung signal from each marked location on the patent recording canvas as (Continued)

merged information, and applies processing to the merged information to generate the asthmatic condition indication.

20 Claims, 22 Drawing Sheets

(51) Int. Cl.
    *G16H 50/20*     (2018.01)
    *A61B 5/145*     (2006.01)
    *A61B 5/00*     (2006.01)
    *A61B 7/02*     (2006.01)
    *G16H 50/70*     (2018.01)
    *G16H 80/00*     (2018.01)

(52) U.S. Cl.
    CPC ............... *A61B 7/02* (2013.01); *G16H 50/20* (2018.01); *G16H 50/30* (2018.01); *G16H 50/70* (2018.01); *G16H 80/00* (2018.01)

(56) References Cited

U.S. PATENT DOCUMENTS

| | | | |
|---|---|---|---|
| 2011/0144451 A1* | 6/2011 | Robertson | G16H 40/67 600/300 |
| 2014/0073880 A1* | 3/2014 | Boucher | A61B 1/227 600/301 |
| 2014/0107515 A1* | 4/2014 | Lee | A61B 7/008 600/528 |
| 2015/0190110 A1* | 7/2015 | Chong | A61B 5/7217 600/528 |
| 2015/0205916 A1* | 7/2015 | Yamamoto | G16H 80/00 702/19 |
| 2015/0230751 A1 | 8/2015 | Yamanaka et al. | |
| 2018/0228434 A1* | 8/2018 | Dwarika | A61B 5/6801 |
| 2018/0317876 A1* | 11/2018 | Emmanouilidou | G06N 99/00 |

* cited by examiner

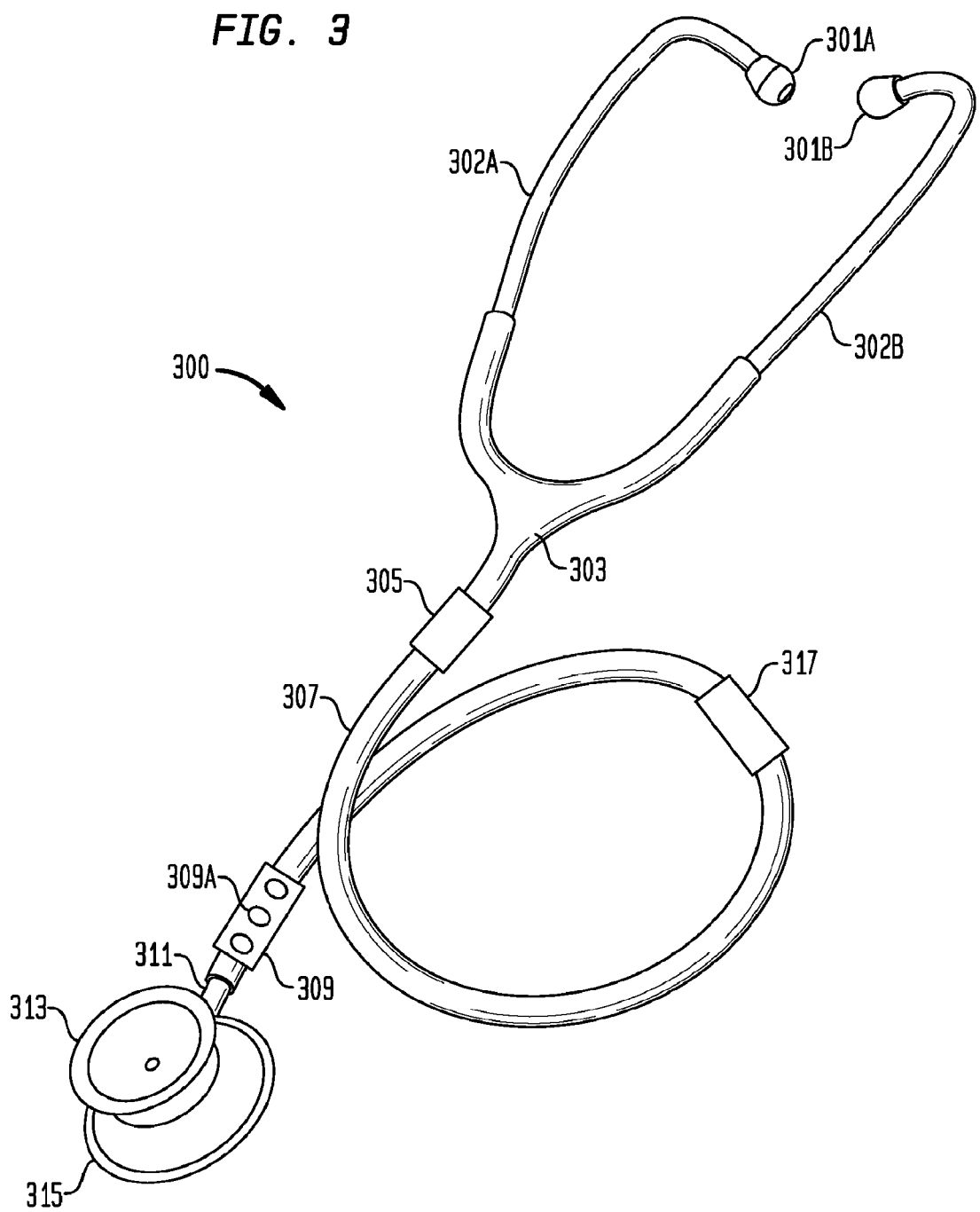

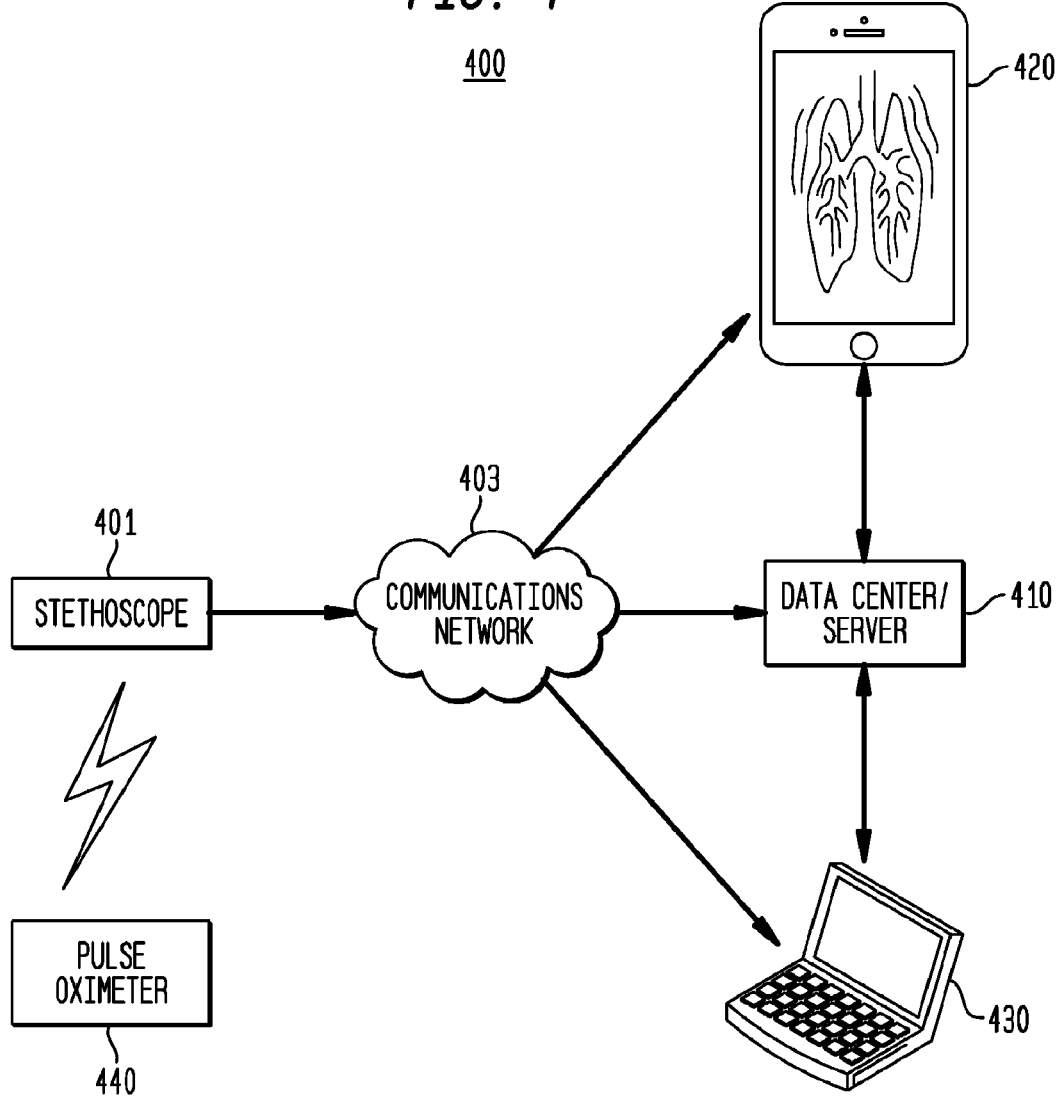

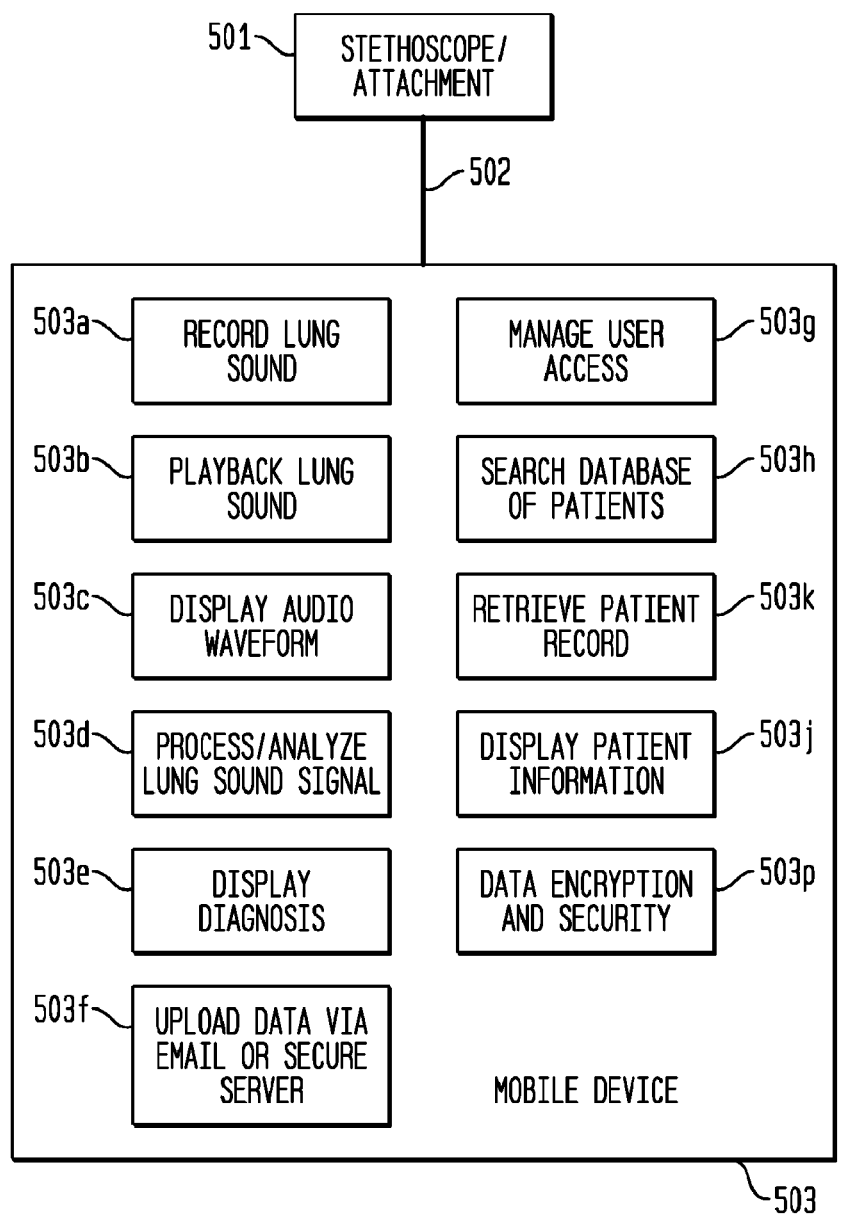

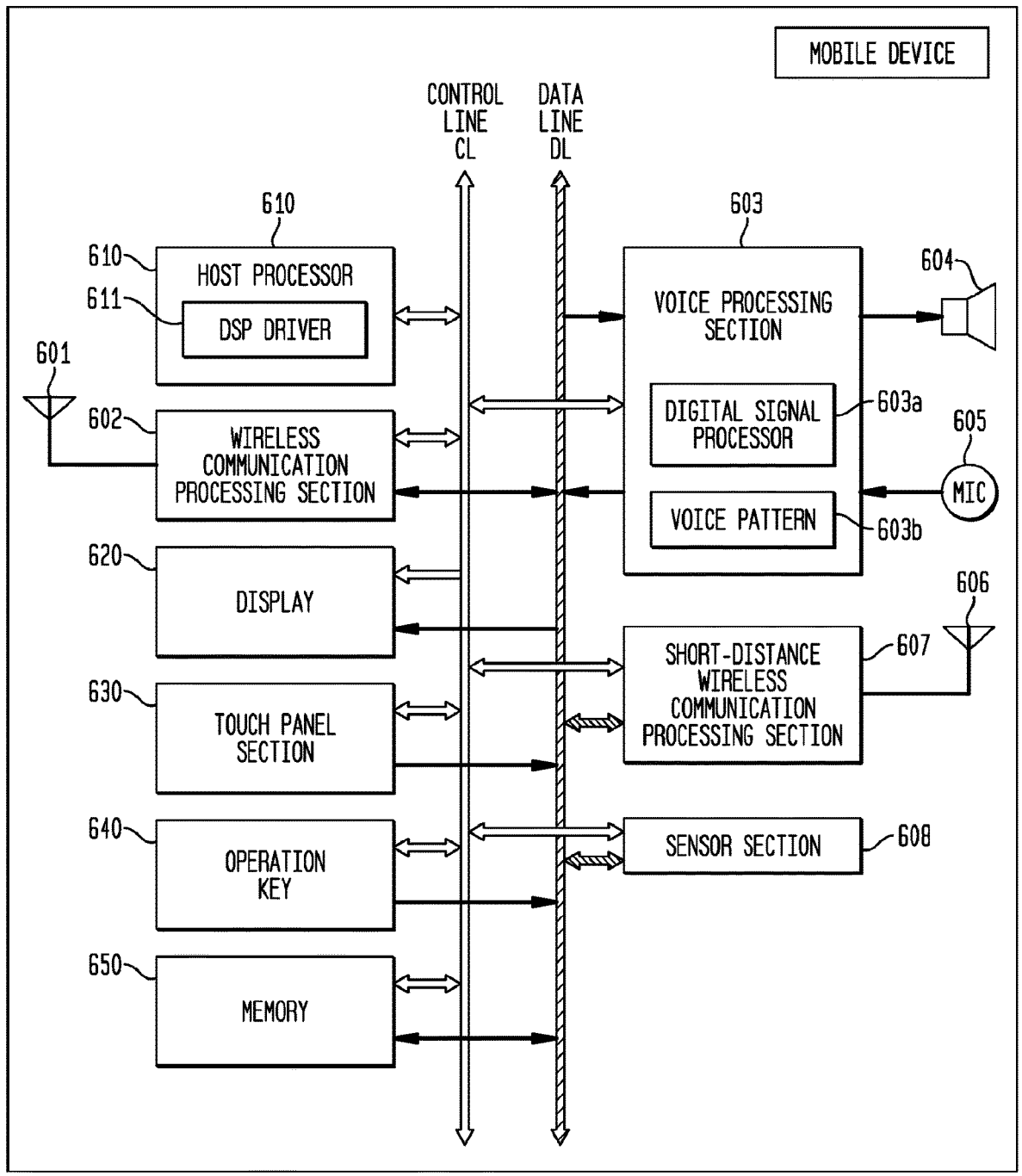

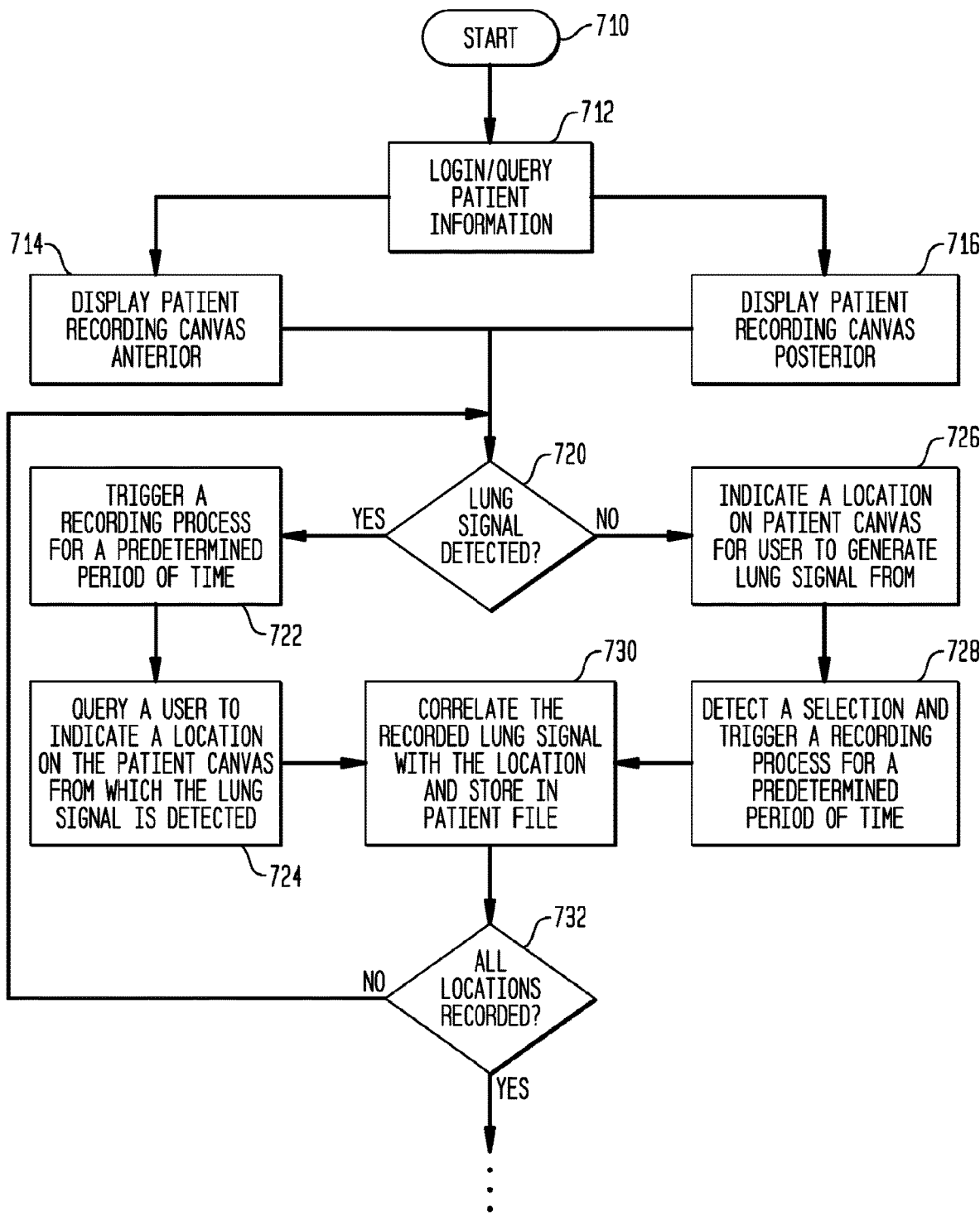

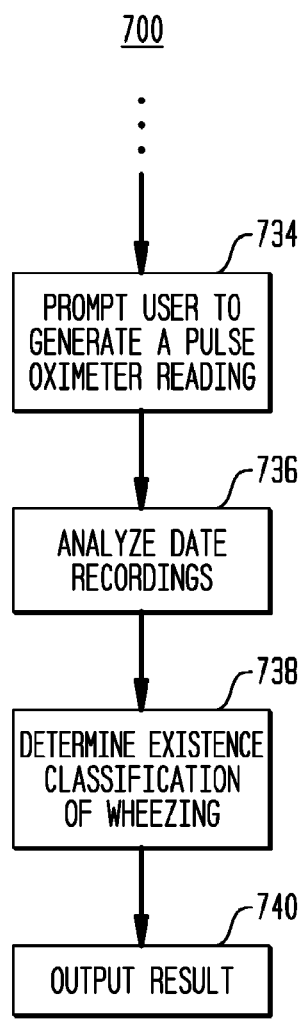

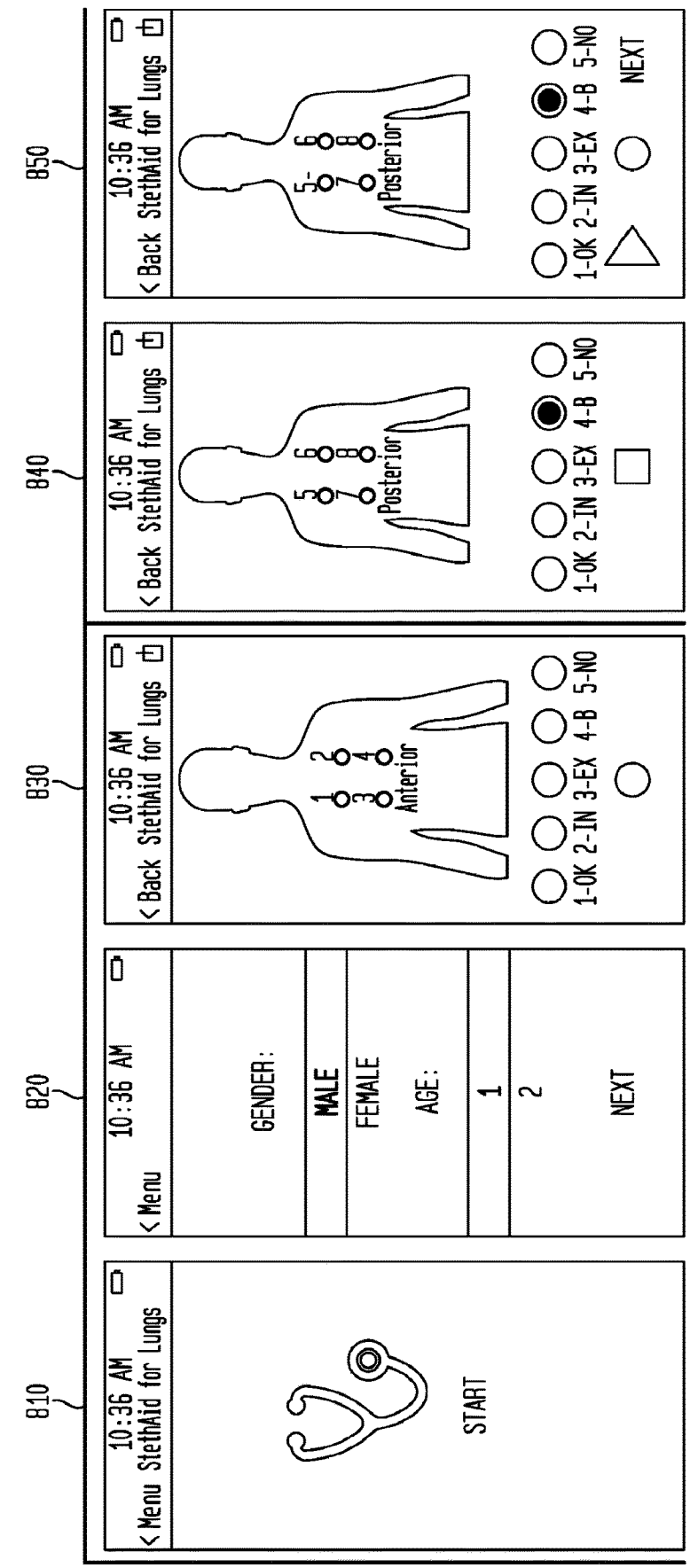

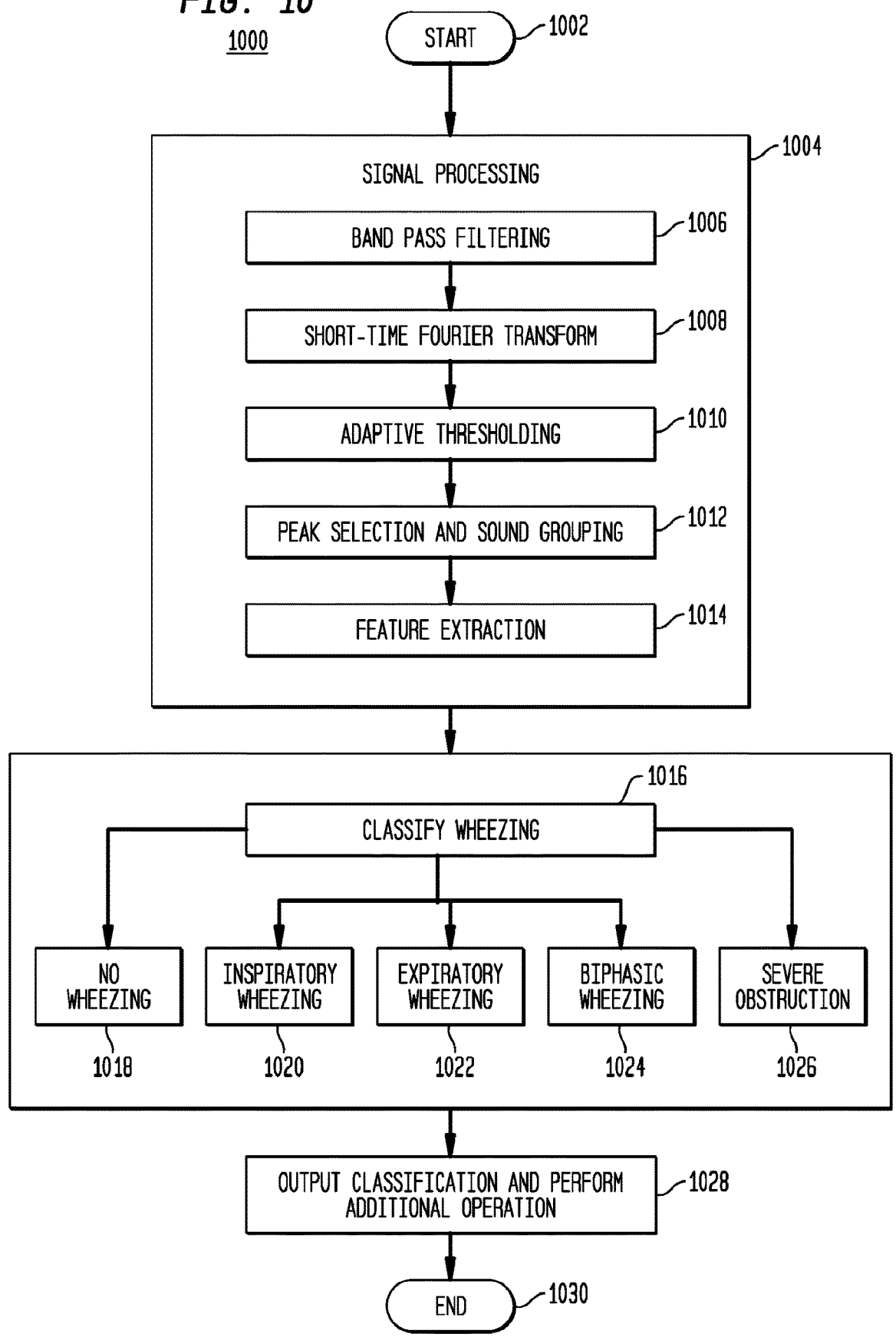

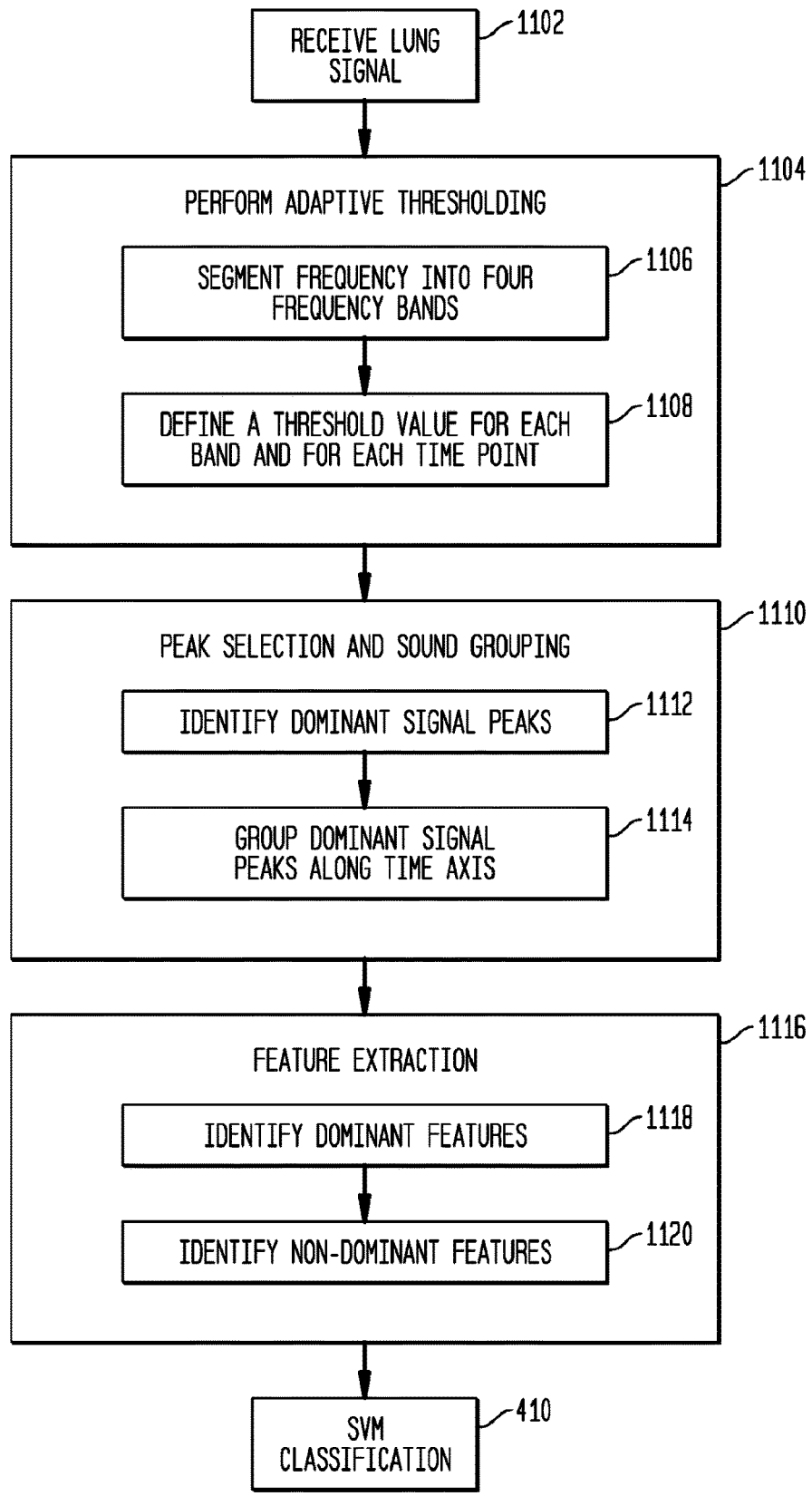

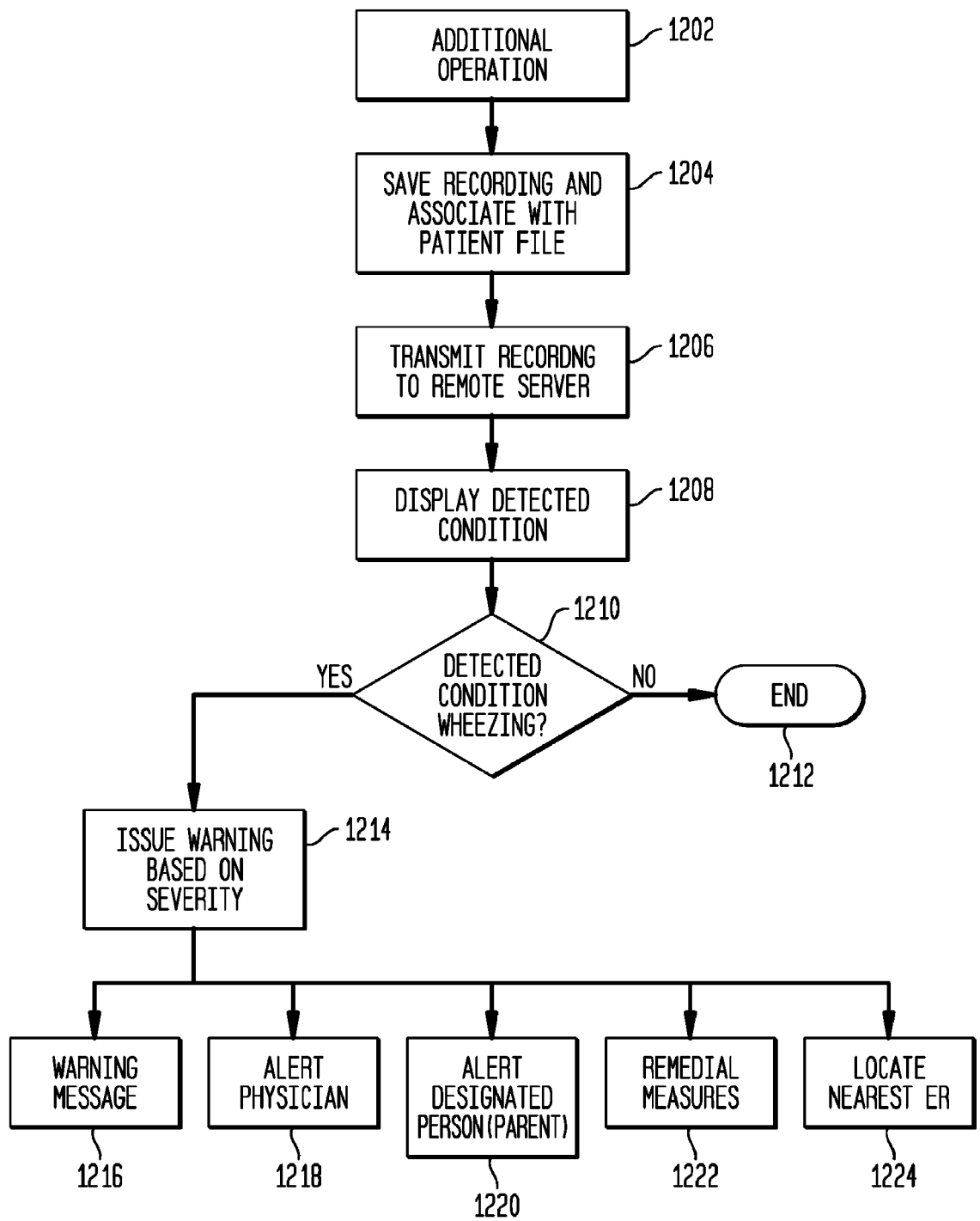

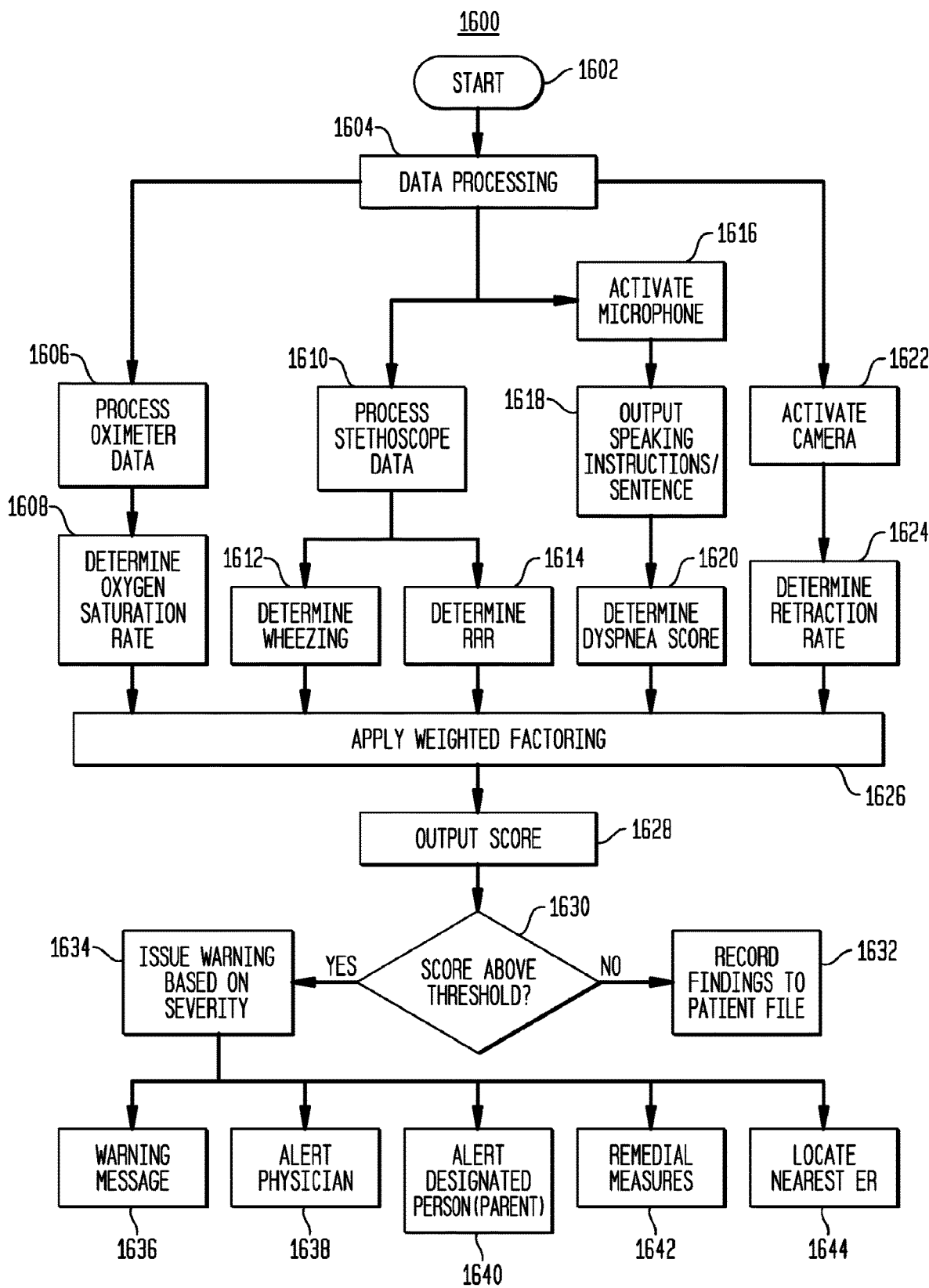

FIG. 17

| CHARACTERISTIC | 0 | 1 | 2 |
|---|---|---|---|
| RESPIRATORY RATE<br>*OBTAIN OVER 30 SEC, MULTIPLY BY 2 | | | |
| 2-3 YEARS | ≤ 34 | 35-39 | ≥ 40 |
| 4-5 YEARS | ≤ 30 | 31-35 | ≥ 36 |
| 6-12 YEARS | ≤ 26 | 27-30 | ≥ 31 |
| >12 YEARS | ≤ 23 | 24-27 | ≥ 28 |
| OXYGEN REQUIREMENT<br>*OBTAIN WITH PT ON RA FOR 2 MINUTES | ≤93% ON RA | 89-92% ON RA | ≤88% ON RA |
| AUSCULTATION | CLEAR BREATH SOUNDS | EXPIRATORY WHEEZES | INSPIRATORY & EXPIRATORY WHEEZES OR DIMINISHED BREATH SOUNDS |
| WORK OF BREATHING<br>- NASAL FLARING<br>- SUPRASTERNAL MUSCLE USE<br>- INTRACOSTAL MUSCLE USE<br>- SUBCOSTAL MUSCLE USE | ≤1 ACCESSORY MUSCLE | 2 ACCESSORY MUSCLES | ≤3 ACCESSORY MUSCLE |
| DYSPNEA | SPEAKS FULL SENTENCES, PLAYFUL, AND TAKES PO WELL | SPEAKS PARTIAL SENTENCES, SHORT CRY OR POOR PO | SPEAKS SHORT PHRASES, GRUNTING, OR UNABLE TO PO |

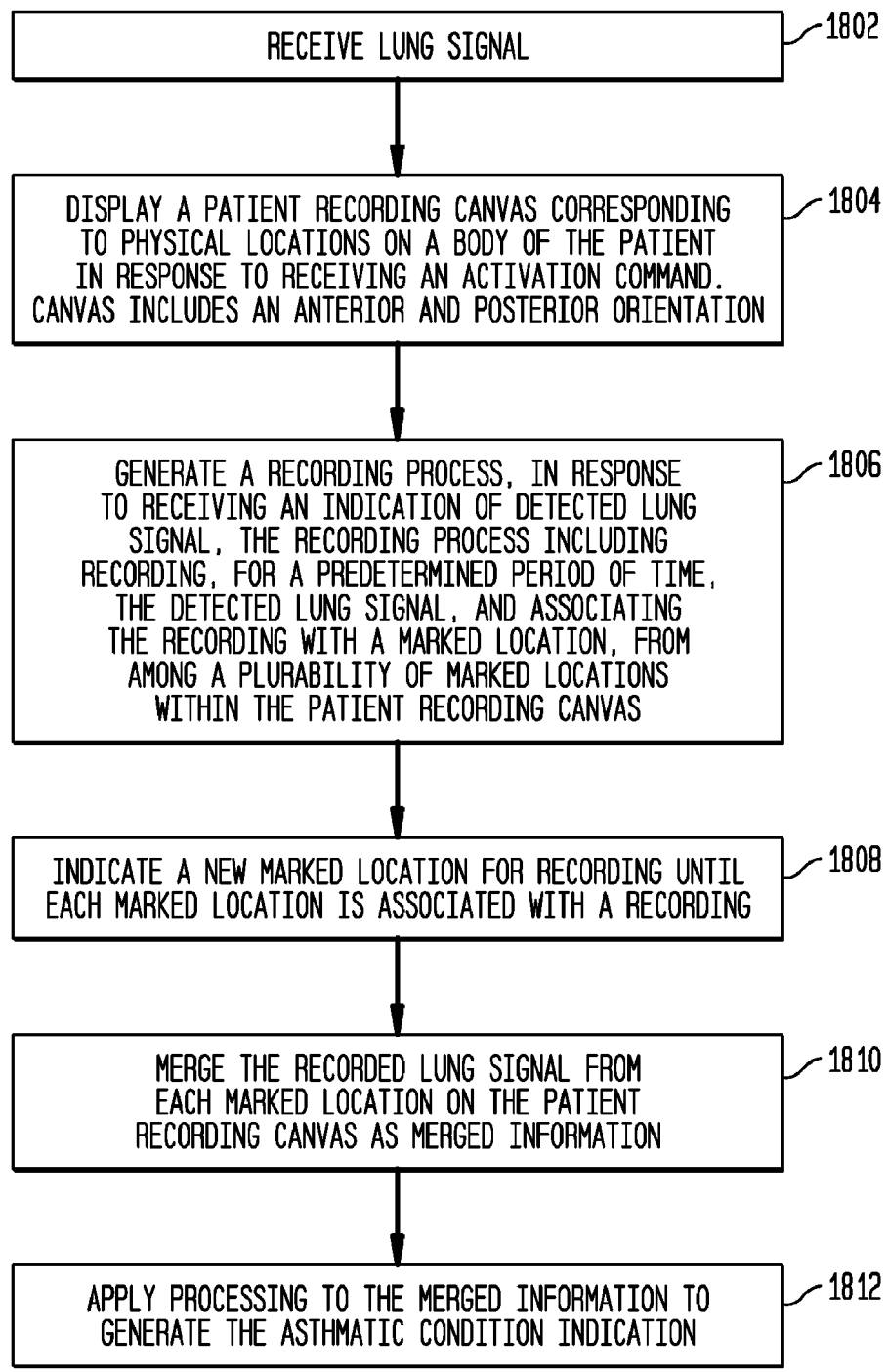

APPARATUS AND METHOD FOR IDENTIFICATION OF WHEEZING IN AUSCULATED LUNG SOUNDS

INCORPORATION BY REFERENCE

The present disclosure claims the benefit of U.S. Provisional Application No. 62/429,605, filed on Dec. 2, 2016, which is incorporated herein by reference in its entirety.

FIELD

The present disclosure relates generally to the field of auscultation, which is a process of listening to the heart, lungs, and gastrointestinal systems in order to assess their functions and detect diseases. Specifically, the present disclosure relates to an apparatus and methods thereof for detecting Wheezing in lungs.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Asthma is a chronic lung disease, occurring in about 10% of children and 8% of adults. It inflames and tightens the airways, and causes wheezing, coughing, breathlessness, and chest tightness. Wheezing is a high-pitch whistling sound made while breathing. It is often associated with difficulty breathing. Wheezing may occur during breathing out (expiration) or breathing in (inspiration).

Without proper management, asthma can results in frequent emergency department (ED) visits, hospitalizations, and premature deaths. In 2010, almost 1.8 million patients visited an ED for asthma-related care and 439,000 people were hospitalized in the United States. The high number of ED visits and hospitalizations underscores that asthma management remains a problem.

Because wheezing has a musical sound quality and a unique auditory characteristic that may not always be detected by visual or in person detection, people with this condition typically would not get medical assistance or seek treatment until the condition worsens or leads to an asthma attack.

Accordingly, there is a need to help asthma patients and families to detect early signs of an impending asthma attach and thus control it. Furthermore, there is a need for a family to avoid going to the doctor for a detection analysis, and instead, can perform detection on demand, at home or any location of their choosing and communicating their finding to the doctor. This in-home detection method can save a patient/parent time and resources that can further be used for care of the patient.

SUMMARY

The present disclosure provides for an apparatus and corresponding methods for detecting wheezing and a level of severity associated with wheezing. Specifically, the disclosure provides for a mobile device based solution that enables primary care physicians, such as pediatricians, family members, such as parents and spouses to successfully identify and diagnose a degree of wheezing.

In one exemplary embodiment of the present disclosure, a computer enhanced medical device for generating an asthmatic condition indication, may comprise an input port configured to receive a lung signal from a stethoscope, the lung signal having been converted from an analog signal to a digital signal; and circuitry configured to in response to receiving an activation command, displaying a patient recording canvas corresponding to physical locations on a body of the patient, the canvas including an anterior patient orientation and a posterior patient orientation. The circuitry may be further configured to in response to receiving an indication of a detected lung signal, generate a recording process, the recording process including recording, for a predetermined period of time, the detected lung signal, and associating the recording with a marked location, from among a plurality of marked locations within the patient recording canvas, indicate a new marked location for recording until each marked location is associated with a recording, merge the recorded lung signal from each marked location on the patient recording canvas as merged information, and apply processing to the merged information to generate the asthmatic condition indication.

In yet another embodiment, the device may store the correlated information in a patient file, indicate a marked location on the patient recording canvas for a user to generate a lung signal from, detect a selection of the location on the patient recording canvas, and trigger a recording process for a predetermined period of time.

In another embodiment, in response to a predetermined number of marked locations on the patient recording canvas not being selected, the circuitry is further configured to indicate an unselected location on the patient recording canvas from which to generate a lung signal.

In another embodiment, the device may also analyze the correlated data, and determine whether the asthmatic condition detected from the correlated data is a wheezing condition, by applying machine learning processing. Additionally, the device may perform a signal pre-processing including performing a filtering operation on the received lung signal, the filtering operation including using a band pass filter configured to filter in a range between 50 Hz and 2000 Hz, and performing a short-time Fourier Transform on the filtered signal, the transform including a 40 ms time window and a window overlap rate of 50%.

The device may also perform adaptive thresholding in different frequency bands by segmenting a frequency axis into four different frequency bands and calculating a threshold value for each frequency band, wherein the threshold is calculated as: Threshold=mean+w *STD, mean being the mean being the average value of data points within the frequency band, w being a weighted factor and STD being a standard deviation value for the data points within the frequency band.

The device may further detect the wheezing condition as being at least one of clear breath sounds (no wheezing), inspiratory wheezing, expiratory wheezing, biphasic wheezing and severely obstructed airway. Upon determining the wheezing condition, the device may further transmit the recordings to a remote server, and output a remedial solution based on the type of detected wheezing condition, and in response to the wheezing condition being a severely obstructed airway, locate a nearest emergency medical facility and output directions to the emergency medical facility.

In yet another embodiment, the device may in response to the wheezing condition being an inspiratory, expiratory or biphasic wheezing condition, transmit an alert message to an electronic device associated with a medical provider, the alert message including the recordings, and transmit an alert message to an electronic device associated with a guardian or caretaker of the patient.

In another embodiment, the device may receive an oximeter signal including oxygen saturation levels, and generate the asthmatic condition information by being configured to determine resting respiratory rate based on the processed lung signal from the stethoscope, determine a Dyspnea score of the patient by activating a microphone within the device, outputting speaking instructions for the patient to speak, detect natural language speech pattern, and output a Dyspnea score, determine a retraction rate by activating a camera within the device, measuring physical symptoms, including chest retractions, based on severity of the chest retractions, output a retraction score, apply a weighted score to the oxygen saturate rate, the wheezing, the resting respiratory rate, the retraction rate and the Dyspnea score, determine and output an asthma score based on the weighted score.

The device may further in response to the asthma score being below a threshold, proceed to save recordings to patient file and transmit a file update to the remote server, and in response to the asthma score being above a threshold, proceed to display a warning and transmit at least one alert message to a physician associated with the patient.

In yet another embodiment, a computer enhanced medical method for generating an asthmatic condition indication, is described, the method including receiving, at an input port of a mobile device, a lung signal from a stethoscope, the lung signal having been converted from an analog signal to a digital signal; in response to receiving an activation command, displaying a patient recording canvas corresponding to physical locations on a body of the patient, the canvas including an anterior patient orientation and a posterior patient orientation; in response to receiving an indication of a detected lung signal, generating a recording process, the recording process including recording, for a predetermined period of time, the detected lung signal, and associating the recording with a marked location, from among a plurality of marked locations within the patient recording canvas; indicating a new marked location for recording until each marked location is associated with a recording; merging the recorded lung signal from each marked location on the patent recording canvas as merged information; and applying processing to the merged information to generate the asthmatic condition indication.

The method further includes in response to not detecting the lung signal, indicating a marked location on the patient recording canvas for a user to generate a lung signal from, detecting a selection of the marked location on the patient recording canvas, and triggering a recording process for a predetermined period of time. Additionally, in response to a predetermined number of displayed locations on the patient recording canvas not being selected, indicating an unselected location on the patient recording canvas from which to generate a lung signal from.

In yet another embodiment, the method further includes analyzing the correlated data, and determining whether the asthmatic condition detected from the correlated data is a wheezing condition, by applying machine learning processing.

Additionally, the method may further include receiving an oximeter signal including oxygen saturation levels; and generating the asthmatic condition indication by determining a resting respiratory rate based on the processed lung signal from the stethoscope; determining a Dyspnea score of the patient by activating a microphone within a mobile device, outputting speaking instructions for the patient to speak, detecting natural language speech pattern, and outputting a Dyspnea score; determining a retraction rate by activating a camera within the mobile device, measuring physical symptoms, including chest retractions, based on severity of the chest retractions, outputting a retraction score; applying a weighted score to the oxygen saturate rate, the wheezing, the resting respiratory rate, the retraction rate and the Dyspnea score; and determining and outputting an asthma score based on the weighted score. Additionally, in response to the asthma score being below a threshold, saving the recordings to patient file and transmitting a file update to the remote server; and in response to the asthma score being above a threshold, displaying a warning and transmitting at least one alert message to a physician associated with the patient.

The foregoing paragraphs have been provided by way of general introduction, and are not intended to limit the scope of the following claims. The described embodiments together, with further advantages, will be best understood by reference to the following detailed description taken in conjunction with the accompanying drawings.

BRIEF DESCRIPTION OF THE DRAWINGS

Various embodiments of this disclosure that are provided as examples will be described in detail with reference to the following figures, wherein like numerals reference like elements, and wherein:

FIG. 3 illustrates an exemplary stethoscope according to an embodiment;

FIG. 4 illustrates, according to an embodiment, a schematic block diagram illustrating a stethoscope system;

FIG. 5 depicts an exemplary block diagram illustrating functions performed by the mobile device;

FIG. 6 illustrates schematically an exemplary mobile phone terminal device;

FIGS. 7A and 7B illustrate, according to one embodiment, a flowchart depicting the steps performed to detect and classify wheezing from a processed lung signal;

FIG. 8 depicts an exemplary mobile application for classifying wheezing in a patient and providing health care solution;

FIG. 10 illustrates, according to one embodiment, a flowchart depicting the steps performed to process a lung signal and wheezing classification;

FIG. 11 illustrates, according to one embodiment, a flowchart depicting the steps performed to process a lung signal and perform a support vector machine (SVM) classification and providing additional medical support after classification is performed;

FIG. 12 illustrates, according to one embodiment, a flowchart depicting the steps performed to process a lung signal and providing additional medical support after classification is performed;

FIG. 16 illustrates, according to an embodiment, a flow chart depicting the steps performed to determine the asthma score and providing health care/medical support based on the detected asthma score;

FIG. 17 illustrates, according to an embodiment, a chart depicting possible parameters and values used to determine the asthma score; and FIG. 18 illustrates, according to an embodiment, a flow chart depicting the steps performed to determine the asthmatic condition based on received parameters.

DETAILED DESCRIPTION

Figure 1:
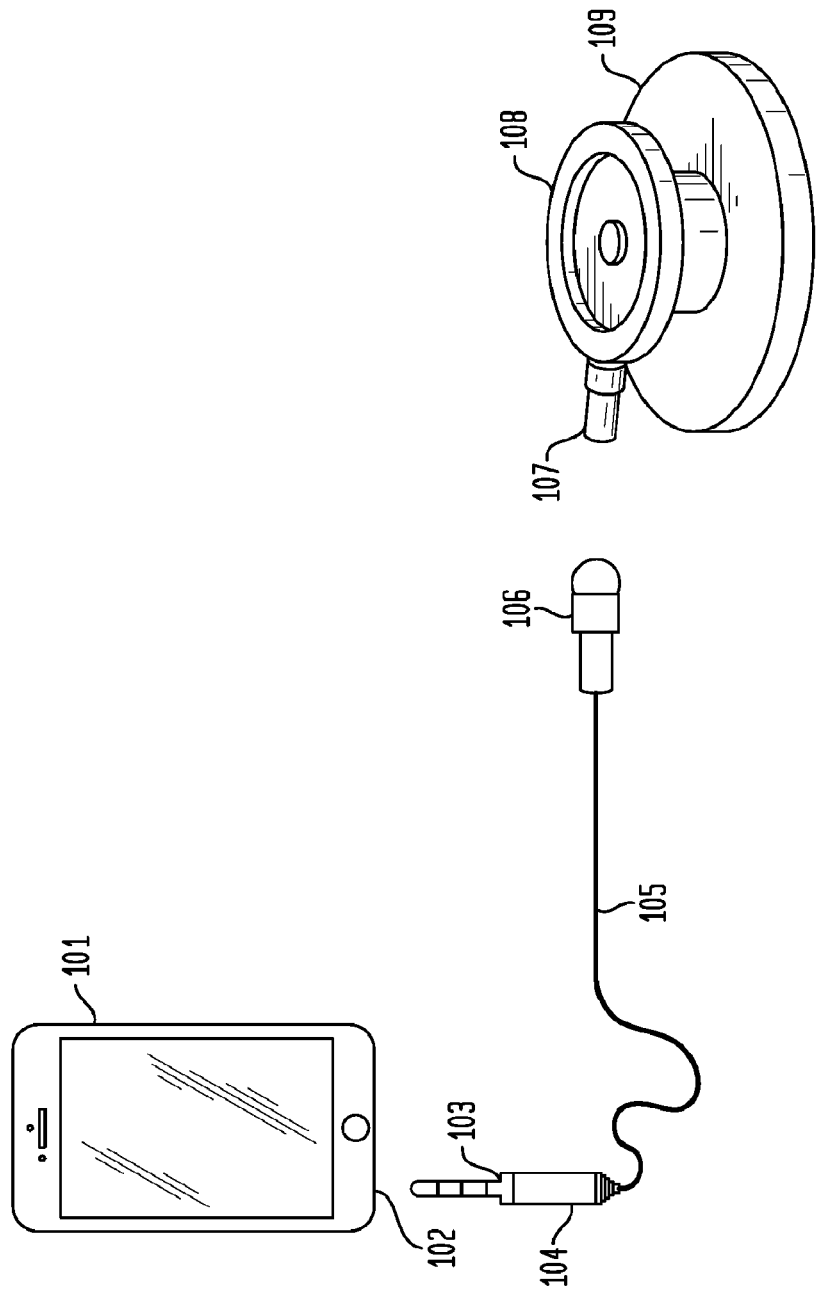
FIG. 1 illustrates, according to an embodiment, a mobile device and a stethoscope attachment.

As envisioned by the described embodiments herein, the present disclosure provides a real time solution to measuring, managing and treating asthma related symptoms including, wheezing detection and treatment. Such detection and treatment methodologies provide medical and technical improvements over existing methodologies in that parents or patients may be able to perform the measurements and diagnostics themselves without resorting to doctor or ER visits at every possible instance. This saves time and money. Additionally, the testing parameters and recordings are of the objective nature and thus, provide high accuracy measurements of asthma related parameters. Such detection devices can then provide real time analysis and diagnostics to a remote medical professional, and/or provide remedial solutions instantaneously. Such remedial solutions are in line with health professional approved methodologies.

As can be appreciated, the chronic nature of the asthma condition requires constant monitoring and treatment for patients. Accordingly, the embodiments of the present disclosure provide a device, system and methodology that enables simple, real time, in home detection of wheezing and other asthma related parameters, communication with a doctor, tracking of the diagnostics, and real time remedial measures.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and devices provided in particular implementations. However, the processes and devices will operate effectively in other implementations. Phrases such as "an embodiment", "one embodiment" and "another embodiment" may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by appended claims.

Furthermore, where a range of values is provided, it is to be understood that each intervening value between the upper and lower limit of the range—and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

FIG. 1 illustrates, according to an embodiment, a perspective view depicting an attachment between a mobile device 101 and a stethoscope. In FIG. 1, the mobile device 101 includes an audio port 102 that is disposed at a lower or upper edge of the mobile device 101. The audio port 102 includes an opening where a microphone lead 103 of a microphone attachment 104 may be inserted. The microphone attachment 104 includes a 3.5 mm cable 105 that is attached to a microphone head/receiver 106. Further, the microphone head/receiver 106 is attached to a stethoscope head 107, which has a bell 108 and diaphragm 109 that can be used for auscultation purposes. In such a manner, the stethoscope, as depicted in FIG. 1, makes an electrical connection (via the microphone attachment) to the mobile device 101. The lung sound received from the stethoscope is converted to an electrical signal (using the microphone attachment 104, cable 105, microphone lead 103, and the microphone head/receiver 106) prior to being received by the audio port 102 of the mobile device 101. It is understood that such implementation is meant as a non-limiting of the attachment between the mobile device and the stethoscope, and other embodiments, including, for example, medical devices, desktop computers and the like, may also be connected to the stethoscope.

Figure 2:
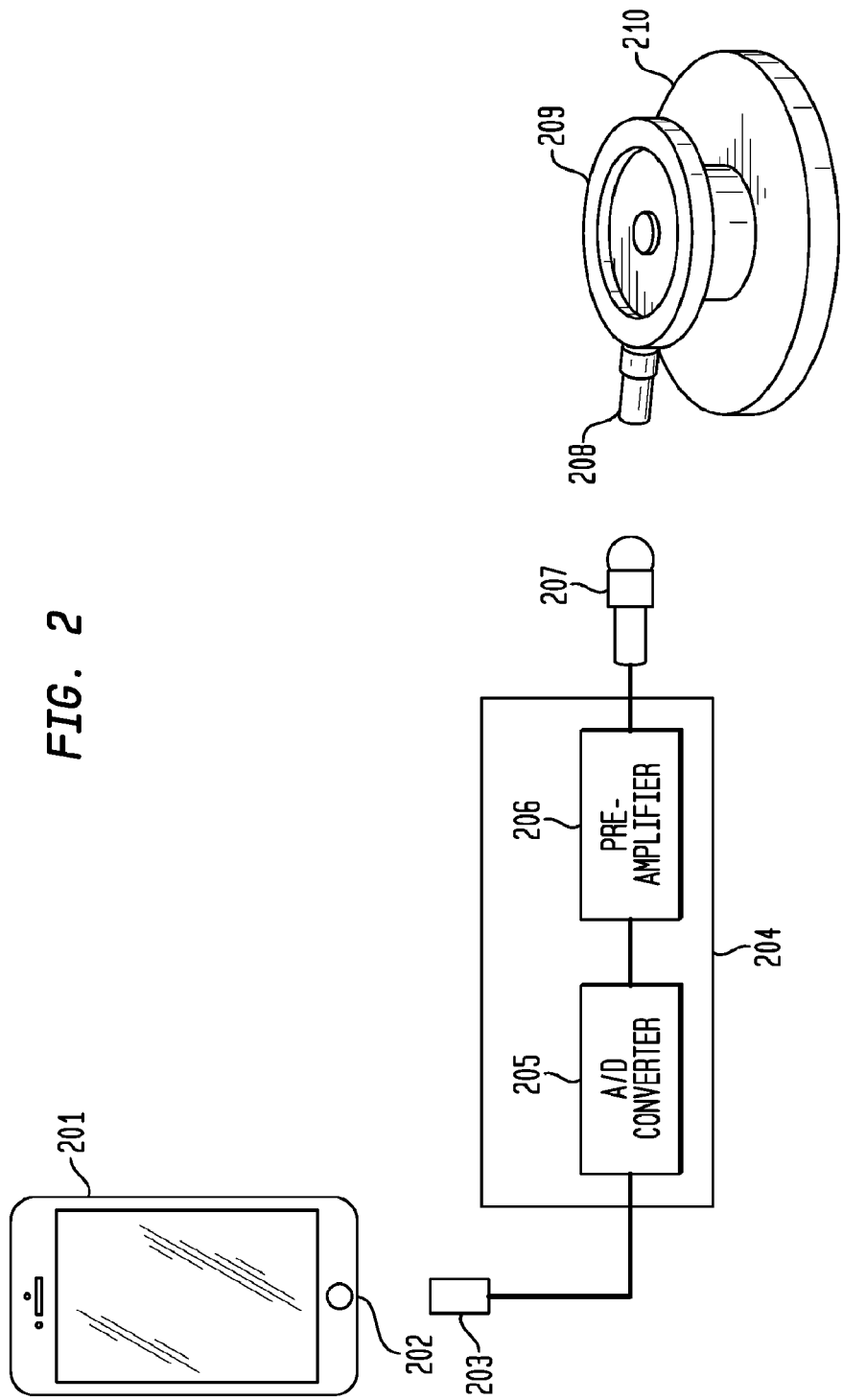
FIG. 2 illustrates, according to an embodiment, a mobile device and another stethoscope attachment.

FIG. 2 illustrates, according to an embodiment, a perspective view depicting an attachment between a mobile device 211 and a stethoscope. In FIG. 2, the mobile device 201 includes a digital port (for example, Micro-USB for android devices or Lightning port for Apple devices) 202 that is disposed at a lower center portion of the mobile device 201. The digital port 202 includes an opening where a Micro-USB or Lighting cable 203 of an attachment 204 may be inserted. The attachment 204 includes A/D converter 205 that is connected to a microphone pre-amplifier 206. The pre-amplifier 206 is connected to the microphone head/receiver 207. Further, the microphone head/receiver 207 is attached to a stethoscope head 208, which has a bell 209 and diaphragm 210 that can be used for auscultation purposes. In such a manner, the stethoscope, as depicted in FIG. 2, makes an electrical connection (via the attachment 204) to the mobile device 201. Instead of digitizing lung sounds from the analog stethoscope using the mobile device 201, the lung sounds can be digitized using an external device (i.e., an attachment 204). The audio circuit on the mobile device may be optimized for human voice. Digitizing the lung sound using mobile devices may not be able to capture the low frequency components of the lung sound. The attachment 204 (including the A/D converter 205 and pre-amplifier 206)

and the microphone head/receiver 207 that can capture the sound from 20 Hz to 1000 Hz may be used.

Each of the mobile devices 101, 201 as shown in FIGS. 1 and 2, respectively, may include a processor (circuitry) and sufficient memory having stored therein one or more sets of instructions, e.g., in the form of a user application or 'app', that is executable by the processor, in order to enable a user of the mobile device to successfully detect and distinguish a wheezing sound from a non-wheezing sound, as well as a degree of wheezing relating to asthma. Details regarding the techniques used to detect a wheezing are described later with reference to FIGS. 7-13.

Examples of mobile devices 101 and 201 that may be used to detect wheezing include, but are not be limited to, smart phones (such as an iPhone), personal communication devices (PDAs), application-specific mobile electronic devices and/or other mobile electronic devices having sufficient memory and computing power to execute a set of instructions that enable a user of the mobile device to successfully detect wheezing. Further, the 'app' installed on the mobile device may also be used as a business development tool. For instance, the 'app' may be used to increase profits by leveraging business development tools contained within the 'app' and/or accessed through the 'app'. For example, two areas of business development may be addressed by the app: 1) increasing sales of the device by offering, demonstrating and proving the effectiveness in successfully detecting wheezing without professional guidance, and 2) increase operational efficiency, and ease of use of the device by providing a stepwise instruction that directs a user in operating the device, thereby reducing overhead costs.

FIG. 3 illustrates an exemplary stethoscope 300 according to an embodiment of the present disclosure. The stethoscope 300 includes a sound receiving chest piece that may include both a bell 313 and an opposed diaphragm 315. According to one embodiment, the bell 313 and the diaphragm 315 may also be collectively referred to as the "chest piece." The bell 313 and diaphragm 315 are integrally-formed and connect by means of a tubular fitting 311 to a flexible tube 307, which includes a yoke 303.

Ear tubes 302A and 302B are connected to the tube 307 through the yoke 303 and include ear-tips 301A and 301B, which are received in the ears of the user. The frequencies detected and amplified by the bell 313 and/or the diaphragm 315 are transmitted through the tube 307 and the ear tubes 302A, 302B to the ear-tips 301A, 301B. The bell 313 and the diaphragm 315 comprise the patient-contacting portions of the stethoscope 300 and are the portions which should be covered and protected against contact with body fluids, tissue and skin.

Additionally, the stethoscope 300 includes a processor 305 and a light emitting diode (LED) panel 309 that includes a plurality of LED lights 309A. The stethoscope 300 also includes a display panel 317 that may be, for example, a liquid crystal display (LCD) panel, an organic electroluminescent (OLED) display panel, a plasma display panel, or the like. The display panel 317 may be used to display lung signals obtained from the bell 313 and the diaphragm 315 of the stethoscope 300.

According to one embodiment, the LED panel 309 includes a red LED, a green LED, and a yellow LED. The processor 305 includes sufficient memory having stored therein one or more sets of instructions, that is (are) executable by the processor 305, thereby enabling a user of the stethoscope 300 to successfully detect and distinguish a wheezing from a non-wheezing condition. Specifically, the signals obtained from the bell 313 and the diaphragm 315 of the stethoscope may be processed by the processor 305, in order to diagnose the existence of and type of wheezing in a patient. According to one embodiment, the LED panel 309 is used to provide a visual indication of the type of wheezing detected. For instance, upon detecting wheezing in the patient, the stethoscope 300 may be configured to turn ON the red LED, whereas upon detecting a non-wheezing condition, the green LED may be activated. In the absence of conclusive data (i.e. more areas need to be examined before making a final determination), the yellow LED may be activated. This allows the detected signals to be classified as either a wheezing condition, a non-wheezing condition or requesting additional examination to be conducted as further described herein below.

In other words, the apparatus and methods described in the present invention distinguish a wheezing from non-wheezing. Further, the apparatus and methods described herein also classify the type of wheezing in order to correlate the condition with a method of treatment. For example, display panel 317 may further display an indication of a clear breath sound (i.e. no wheezing), inspiratory wheezing, expiratory wheezing, biphasic inspiratory and expiratory wheezing, and no audible airflow or severely obstructed airway. Based on these detected classifications, a remedy, method of treatment, or recommendation may further be output to the patient. For example, if a severely obstructed airway is detected, the processor 305 may provide further instructions of care, such as an indication that the patient needs to visit a medical facility or emergency department (ED) or seek immediate medical assistance, or the like. Hereinafter, the terms emergency department, ED, emergency room, ER or the like are used synonymously and are implied to mean a medical facility that can treat the patient or provide medical care. Similarly, the terms doctor, nurse, medical professional or the like are used synonymously and are implied to mean a medical professional that is certified to provide treatment to the patient.

FIG. 4 illustrates, according to an embodiment, a schematic block diagram illustrating a stethoscope system 400. The system 400 includes a stethoscope 401 that is configured to receive lung signals from a patient. The signals obtained by the stethoscope 401 may be processed either by a mobile device that is connected to the stethoscope 401 (as shown in FIGS. 1, 2A, and 2B), or alternatively, the lung signal may be processed by a processor (circuitry) that is built-in the stethoscope as shown in FIG. 3.

By one embodiment, the stethoscope 401 may communicate with a data center (server) 410 via a communications network 403. The stethoscope 401 may use transmission control protocol/Internet protocol (TCP/IP), user datagram protocol (UDP) or the like for transmission of medical information (patients' health record, heart and/or lung signal, etc.) to the data center 410. Additionally, the data center 410 may include an applications server that is configured with web applications and client specific applications as needed for the organizing/maintaining and sharing of client information with medical professionals. In addition, the applications server may communicate with the communication network 403 via a router and be further protected and buffered by a firewall.

The stethoscope 401 may also be configured to transmit the detected lung signal to a mobile device 420 using the communication network 403. For instance, the stethoscope (via the communication network 403) may implement a packet switching approach such as connectionless packet switching (datagram switching) or a connection-oriented packet switching (virtual circuit switching) to transfer information to the mobile device 420. In a similar manner, the stethoscope 401 may also use the communication network 403 that may be a local area network (LAN) to transfer information to a workstation 430. Additionally, the workstation 430 may include a web-browser that facilitates communication with the application server included in the data center 410. Furthermore, the mobile device 420 may access the communication network 403, as well as communicate with the application server included in the data center 410 with a compatible web-browser or any user interface. In this manner, the data center 410 may provide client specific data upon demand.

The stethoscope 401 may also be configured to communicate with a pulse oximeter, such as, for example, a Nonin Model 3230 pulse oximeter, in order to obtain oxygen saturation data. Oxygen saturation is a measure of how much oxygen a patient's blood is carrying at a particular point in time. During an asthma attack, oxygen saturation levels may drop below an acceptable threshold. As will be further described herein, oxygen saturation levels may be used to determine an overall asthma score. Beyond determining wheezing, determining an overall asthma score can help a medical professional make a determination as to what remedial measures may be further taken. For example, a situation where wheezing is detected but oxygen saturation levels fall within acceptable limits may lead to a lower asthma score and thus, the system may convey to a doctor, or the system itself may provide a solution based on the asthma score. Alternatively, if the detected oxygen saturation levels fall outside the acceptable limits, then a higher asthma score is likely to be calculated and a different remedial measure may be recommended.

It must be appreciated that additional and/or alternative configurations of the stethoscope system as described above are well within the scope of the present disclosure. For instance, in the case of the stethoscope having a built-in processor (processing circuitry) and a display panel as shown in FIG. 3, the stethoscope may communicate with the data center, workstation, and/or other mobile devices to receive medical information pertaining to a particular user. Additionally, the stethoscope 401 may communicate directly with a mobile device 420 through wireless technology, such as Bluetooth or WiFi or the like, and transmit/receive data directly to/from the mobile device 420.

FIG. 5 depicts an exemplary block diagram illustrating the functions performed by a mobile device pertaining to the lung sound (signal). Hereinafter the terms lung sound and lung signal are used synonymously and are implied to mean a signal obtained from the stethoscope placed on a patient's chest or other device that obtains lung related signals.

According to an embodiment, a stethoscope may be attached via a stethoscope attachment 501 to the mobile device 503. Thus, the stethoscope can capture audio signals, for instance, lung signals, and transfer the audio signal 502 to the mobile device 503 for further processing.

FIG. 5 depicts, according to an embodiment, applications that may be executed by the mobile device 503 in processing the lung signal that is transferred from the stethoscope. The hardware components of the mobile device 503 that execute the applications are described later with reference to FIG. 6. The applications can be accessed by a user via a user interface.

A lung sound captured by the mobile device may be recorded 503a and saved in memory of the mobile device 503 for further processing. Additionally, the lung signal stored in the memory of the mobile device may be retrieved by a processor (processing circuitry) of the mobile device to be played back 503b at a later time instant. Thus, in this manner, the mobile device can retrieve a previously stored lung signal of a patient and compare the stored lung signal with a current lung signal of the patient and perform an analysis, such as a comparison, progress determination and the like. The mobile device 503 is also configured to display a waveform 503c corresponding to the lung sound on a display panel of the mobile device.

By one embodiment, the mobile device processes (and analyzes) the lung signal 503d to determine whether the lung signal includes wheezing. Details regarding the processing performed by the mobile device to detect the presence of wheezing are described later with reference to FIGS. 10, 11 and 12. Additionally, the mobile device 503 is also configured to display diagnostic information 503e pertaining to the processing of the lung signal. Such diagnostic information may be displayed on the display panel of the mobile device. Details regarding to the display of diagnostic information, providing medical advice and remedial measures, and communication with a medical professional are described later with reference to Figs.

According to one embodiment, the mobile device 503 is also configured to perform communicative as well as organizational functions related to the lung signal. For instance, the mobile device may upload the lung signal 503f stored in the local memory of the mobile device to a remote server, for instance, via an email application, direct peer-to-peer communication with the server, via a cloud based application, and the like. The mobile device 503 may implement email protocols such as POP, IMAP and SMTP or the like, to email medical information of the user. Additionally, the mobile device 503 may use encryption techniques 503p such as hashing, symmetric cryptography, and asymmetric cryptography to transfer information from the mobile device 503 to the server and/or another mobile device.

Additionally, upon connecting with the remote server, the mobile device 503 may query the server to perform a search operation (for example, search a database of patients 503h) in order to retrieve information belonging to a particular user. In one embodiment, the remote server may have a dedicated database that stores patient information as individual records. The mobile device 503 may communicate with the remote server in order to retrieve a particular patient's medical information (record) 503k. Upon retrieving the patient's record, the mobile device 503 may display the record 503j on the display panel of the mobile device.

In one embodiment, each of the above stated functionalities may be performed by the mobile device 503 in the form of a user application or 'app', which is executable by the processor of the mobile device. Furthermore, the 'app' may also provide a way to create and manage user access 503g, by creating a secure account and preventing fraudulent attempts to access a user's record as will be further described herein. Although applications 503a to 503p are described above, it should be noted that other applications commensurate with the scope of the description can be executed by the mobile device 503. For example, applications to review and edit the lung signals, to provide guidance, support and diagnostics of patient data prior to or instead of visiting a hospital, ER or ED, to allow user entry of patient information via a user interface, to store information, to transmit information, and other related applications can be executed by the mobile device 503.

FIG. 6 illustrates a schematic block diagram of an exemplary mobile phone terminal device 600. The hardware components as depicted in FIG. 6 may be configured to perform the processing functions described with reference to FIG. 5. As shown in FIG. 6, the mobile phone terminal device 600 may include an antenna 601 and a wireless communication processing section 602. The wireless communication processing section 602 may communicate wirelessly via radio signals, or the like, with other mobile devices via a base station. Further, a data signal, such as a voice transmission from another user, may be received by antenna 601 and sent to the wireless communication processing section 602 for further processing. In the case of an incoming voice transmission, the voice data signal may be sent from the wireless communication processing section 602 to a voice processing section 603. Incoming voice data received by the voice processing section 603 via the wireless communication processing section 602 may be output as sound via a speaker 604.

Conversely, an outgoing voice signal may be supplied by a user to the voice processing section 603 via a microphone 605. The voice signal received via microphone 605 and processed by the voice processing section 603 may be sent to wireless communication processing section 602 for transmission by the antenna 601. The voice processing section 603 comprises a digital signal processor (DSP) 603a which digitizes the incoming analog signal and processes the audio input to detect for keywords. Keywords enable the operation of device 600, when it is configured to operate under the instructions of specific voice commands. These keywords are preset in the device with the aid of a voice registration circuit and stored in the voice pattern library 603b.

A second antenna 606 may be supplied for use with a short distance wireless communication processing section 607. The short distance wireless communication processing section 607 may communicate wirelessly with other devices over a network, such as the Internet, a local area network (LAN), or a wide area network (WAN). The second antenna 606 may, e.g., by a WiFi transceiver.

A sensor section 608 may be provided for the mobile phone terminal device 600. The sensor section 608 may be a motion sensor that detects a motion of an object in the proximity of the mobile phone terminal device 600. The motion may correspond to a user moving an instruction object, such as a finger or stylus, in the proximity of the mobile phone terminal device 600 for the purpose of selecting data displayed on display 620. The motion sensors may enable users to select a portion of a waveform (displayed on a display panel), e.g., a waveform corresponding to wheezing and to further analyze/extract signal features from the selected signal portions.

The mobile phone terminal device 600 may include display 620. The display 620 may be, for example a liquid crystal display (LCD) panel, an organic electroluminescent (OLED) display panel, a plasma display panel, or the like. The display 620 may display text, an image, a web page, a video, or the like. For example, when the mobile phone terminal device 600 connects with the Internet, the display 620 may display text and/or image data which is transmitted from a web server in Hyper Text Markup Language (HTML) format and displayed via a web browser. The display 620 may additionally display data stored in a memory 650.

A touch panel section 630 can detect a touch operation on the surface of the display 620. For example the touch panel 630 can detect a touch operation performed by an instruction object such as a finger or stylus. Touch operations may correspond to user inputs such as a selection of an icon or a character string displayed on the display 620. The touch panel section 630 may be an electrostatic capacitance type device, a resistive type touch panel device, or other such type devices for detecting a touch on a display panel.

The touch panel section 630 may perform processing related to touch operation classification. For example, the touch panel section 630 may assign a predetermined function to be performed when a "tap" touch operation is detected. Similarly, the touch panel section may analyze a touch operation in which the instruction object makes continuous contact with the display 620 while moving the instruction object around the display 620 (e.g., a "swipe" operation). The touch panel section 630 may output a signal based on a classification of the touch operation performed. The signal may for example include information indicating the touch operation classification, the location on the display 620 where the touch operation was performed, and the operation to be performed based on the touch operation.

Data which is detected and processed by the touch panel 630 can be transmitted to a host controller 610. The host controller/processor 610 (processing circuitry) may include one or more processor units (circuits) and can control each element of the mobile phone terminal device 600 based on data detected by the touch panel 630, or by inputs received from operation key 640. The operation key 640 may receive inputs, e.g., from external control buttons included with the mobile phone terminal device 600. The external control buttons may for example control the volume, the power, or a hold operation for the mobile phone terminal device 600.

The host controller 610 may further execute instructions stored in the memory 650. The controller may further comprise of a DSP driver 611, which is configured to communicate with the DSP 603a. Specifically, the driver may actuate the DSP during a voice registering phase, or the DSP 603a may initiate communication with the driver upon the successful detection of a voice command. The driver 611 may further activate the host processor to execute a certain application based on the received voice commands. To this end, the memory 650 may be a non-transitory computer readable medium having instructions stored therein for controlling the mobile phone terminal device 600. Further, the controller 610 may include one or more processors for executing the instructions stored on the memory 650.

The mobile phone terminal device 600 can include a control line CL and a data line DL as internal bus lines for communication. The control line CL can be used to transmit control data from the controller 610. The data line DL may be used for the transmission of voice data, display data, or the like, throughout the various elements of the mobile phone terminal device 600.

FIGS. 7A and 7B illustrate, according to one embodiment, a flowchart depicting the steps performed to detect and classify wheezing from a processed lung signal. Considering FIG. 7A, an application program installed on a mobile device, such as mobile device 600 may be initialized 710. A user may then be prompted to either login or enter patient information for a new user account 712. A login operation may further involve retrieving information from, or establishing a communication with a data center/server such as data center/server 410. It must be appreciated that additional and/or alternative configurations of data retrieval as described above are well within the scope of the present disclosure. For instance, in the data center information may be preloaded onto the mobile device (e.g. mobile device 600) in order to expedite the login/authentication processing. In such a case, the patient information may be retrieved directly from the mobile device memory (e.g. memory 650). In such a case, mobile device 600 may perform periodic syncing with a data center/server to update patient information. Other syncing measures may also be performed, such as dock syncing and the like.

After a login operation is performed, a patient recording canvas may be displayed to the patient or person associated with the patient, such as a friend or a parent or the like. The patient recoding canvas may display an anterior canvas 714 or a posterior canvas 716. The determination of which canvas is to be provided may be based on retrieved patient information (e.g. patient's last diagnosis was done on anterior side and thus would display the opposite side) or it may be preselected for the patient, or the patient may make the selection manually. One objective behind the patient recording canvas is to display patient locations from which readings are to be extracted in making a determination of whether wheezing exists or not. The number of locations is a sample size that, as a whole, provides the most accurate diagnosis with the least number of locations. For example, the sample size in this regard may be four anterior locations and four posterior locations. Alternatively, other sample sizes may be implemented based on user preferences, doctor instruction, or previous condition of the patient. For example, the patient may be known to have a severe asthma, and so fewer locations may be necessary to detect the wheezing.

Patient detection locations may be set to detect wheezing. Additionally, the locations may further be set to determine the location from which wheezing is detected. In this regard, this may assist a medical professional in determining which part of the lung is affected and what remedial measures are would be necessary based on the location.

Next, a determination is made as to whether a lung signal is detected 720. If mobile device 600 detects an incoming lung signal from stethoscope 501, for example, mobile device 600 triggers a recording process 722 for a predetermined period of time to record the incoming signal. Since the location from which the lung signal has not yet been determined, after recording is complete, mobile device 600 may then query the user/patient to indicate the location of the patient recording canvas. When the location indication is received, mobile device 600 then correlates 730 the recorded lung signal with the location and stores the correlated recording the patient electronic file. The patient file, including the recordings and observations, as further described herein, may then be sent to the patient's doctor, data center/server 415 or the like for further storage and/or processing.

If a lung signal is not detected, this means that the stethoscope is not yet placed on a patient body location. Accordingly, DSP 610 of mobile device 600 may indicate a location be indicated on the patient recording canvas displayed on the screen as a location from which a signal is to be generated. This location may be a predetermined location based on the patient profile, or may be a preselected location stored in memory 650 and output by DSP 610. The indication of the location may done through some type of animation, such as a highlight or a blinking light or the like, indicating that the blinking location, for example, is where the patient or a user other than the patient needs to place the stethoscope in order to generate the lung signal. Thereafter, mobile device 600 may detect 728 a user selection and trigger a recording process for a predetermined period of time. In this regard, a user selection may be a confirmation of the location (i.e. user touches the blinking location) or may be a different user selected location. Similarly, once the recording for a predetermined period of time is made, the recorded data is then correlated 730 with the location and stored in the patient file for further processing.

It must be appreciated that additional and/or processing techniques and configurations as described above are well within the scope of the present disclosure. For instance, while in one embodiment DSP 610 may automatically detect a lung signal and begin a recording, in another embodiment, DSP 610 may display a record button enabling a user to select when to start the recording, based on the placement of the stethoscope on the indicated/animated location.

Next, DSP 610 determines 732 whether a recording has been received for all locations necessary to make an accurate wheezing determination. As previously indicated, a number of locations would be necessary to provide an accurate determination of wheezing and the locations where wheezing may be heard. This enables the determination of not just wheezing, but where in the lung wheezing may be generated. If there remains to be locations that have not been recorded yet, the process starts again at step 720 and determining whether a lung signal is detected. At this point, DSP 610 may output a location that has been deemed as not receiving a recording and querying the user to generate the lung signal, as described herein.

If all recordings have been performed, a process according to FIG. 7B is performed.

A pulse oximeter reading is used to determine a value of oxygen saturation levels in the patient's body. This may not have a bearing on the determination of wheezing, but it has a bearing on an asthma score that is later generated for the patient. Accordingly, based on whether the asthma score is to be generated, mobile device 600 may prompt the user to generate a pulse oximeter reading by attaching a pulse oximeter device to the patient's finger. The pulse oximeter device reading may be detected through a plurality of means, including, for example, wireless means, such as WiFi, Bluetooth, infrared technology or the like. Once received, mobile device 600 analyzes the data recordings 736 and determines 738 the existence of and classification of wheezing condition. Thereafter, mobile device 600 outputs the result 740 to the user. As described herein, the result may further be saved in the user profile and shared with the patient's doctor. This can be done in real time, or the system may simply submit the file to a data center/server associated with the doctor for later evaluation.

FIG. 8 depicts an exemplary mobile application 800 for classifying wheezing in a patient and providing a health care solution. Application 800 may be stored in memory 650 and activated by DSP 610 upon user selection or upon detection of a stethoscope signal/attachment to mobile device 600. As previously described, once the application is initialized 810, a login page may be displayed in which a patient may input login information if the patient is a returning user, or a new user screen 820 may be displayed in order to register the patient as a new user.

Once the login process is completed, mobile device 600 may display on, for example, the touch panel 630, a patient recording canvas 830 including patient canvas locations from which a lung signal is to be processed and recorded. Mobile device 600 may also display an anterior side or a posterior side and locations from which lung signal is to be generated. Once a reading is made for a predetermined period of time through a detected lung signal, mobile device 600 then may indicate a detected wheezing for that specific location from which the reading was made. As previously described, a wheezing may be detected from each and/or any location of the patient recording canvas. Once the wheezing condition is detected, or the reading has been done for a predetermined period of time by processing the lung signal, the patient recording canvas 850 may allow the patient to replay the sound, re-record the signal, store the signal, and/or move on to the next detected location.

Figure 9A:
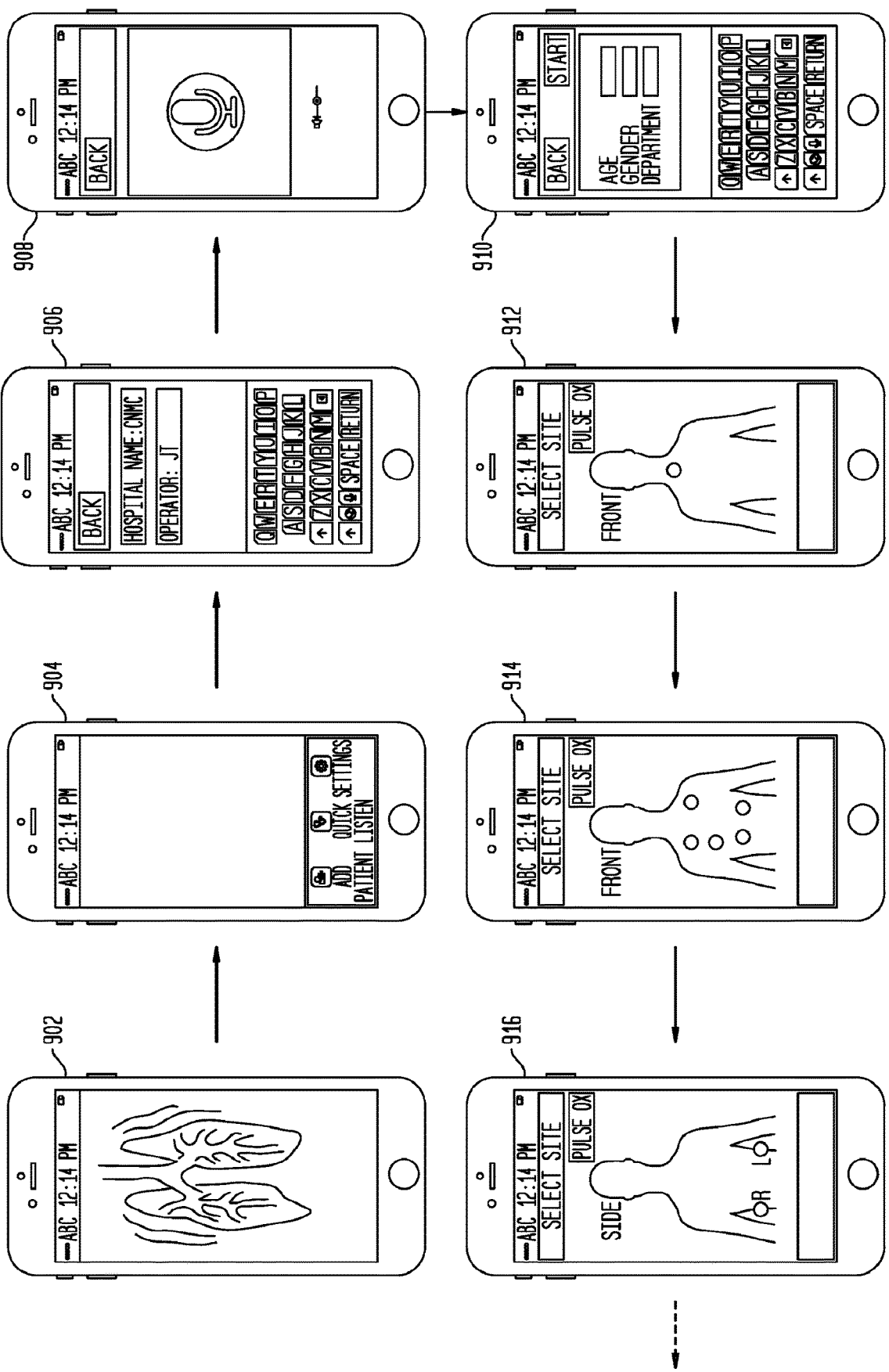
FIGS. 9A and 9B depict exemplary embodiments for registering a patient, providing instructions for detection, detecting wheezing and providing health care solution.
Figure 9B:
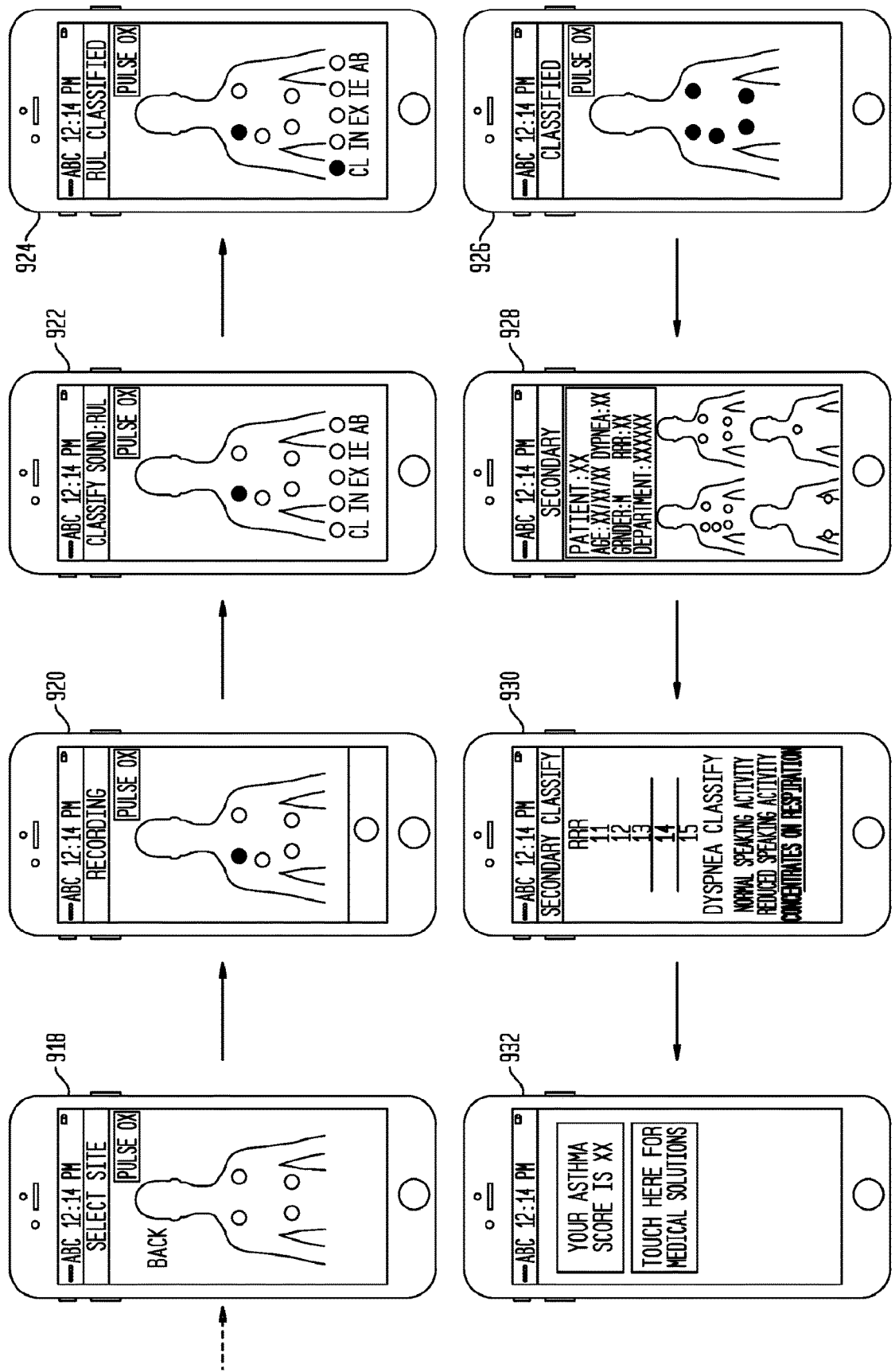

FIGS. 9A and 9B depict exemplary embodiments for registering a patient, providing instructions for detection, detecting wheezing and providing health care solution. As described herein, using the stethoscope generated data, DSP 610 may lunch an application to perform the signal processing of the generated lung signal and provide a patient with a diagnosis and additional medical assistance and/or remedial measures based on the diagnosis as will further described herein. A patient may be registered as previously described and as indicated by screenshots 902-910. Screens 912-916 illustrate a site selection from within the patient recording canvas. As can be understood, the site selection is based on predetermined locations that may yield the most accurate assessment of wheezing, from anterior and posterior locations. Other naming methodologies may be deployed, such as front and rear or side if a patient does not understand anterior and posterior naming methodology.

Turning now to FIG. 9B screens 918-924 describe a site selection, processing and recording of lung signal data associated with the selected side. Thereafter, the lung signal may be classified as a no wheezing or a type of wheezing as will be further described herein. Once all the sites have been processed (screen 926), a review/summary page may be shown 928 in which the patient data may be reviewed. At screen 930, a patient may be given the option to determine an asthma score. This may be optional or may be generated from received data automatically. As will be described herein, an asthma score may depend on a plurality of factors, including the presence of wheezing, in addition to other conditions, such as Dyspnea, oxygen saturation data, and other factors such as resting respiratory rate (RRR). At screen 932, mobile device 600 may output an asthma score along with additional medical recommendations/ remedial measures, depending on the score.

FIG. 10 illustrates, according to one embodiment, a flowchart depicting the steps performed to process a lung signal and wheezing classification. A lung signal may be automatically detected or generated based on placement of the stethoscope on a position/location within the patient recording canvas (i.e. location on patient body corresponding to that of the patient recording canvas). Once the signal is received 1002, a signal processing technique 1004 is performed to extract the wheezing features and classify the wheezing 1016 according to specific categories. Once the wheezing condition is classified, the classification is then output by mobile device 600 and an additional operation may be performed 1028 before the process is ended.

Signal processing 1004 may include band pass filtering 1006 that is performed on the received lung signal. Band pass filtering may include selecting a frequency band that is ideal for detecting peaks associated with a wheezing condition as will be further discussed herein, with respect to FIG. 11. After the lung signal is filtered, a short-time Fourier Transform (STFT) 1008 is performed on the signal and an adaptive thresholding process 1010 is performed on the transformed signal. After thresholding is performed, peak selection and sound grouping 1012 is performed followed by feature extraction 1014. Signal processing will be further described with reference to FIG. 11.

It must be appreciated that additional and/or alternative signal processing techniques and configurations as described above are well within the scope of the present disclosure. For instance, different frequencies, transforms, thresholding and peak selection techniques may be utilized along with the selection of fewer or additional features for extraction may be deployed to detect a higher level of accuracy for wheezing. Additionally, or in the alternative, a machine learning algorithm may be deployed using pattern recognition techniques to identify wheezing. Such algorithm would be deployed to mine large sets of data collected throughout the hospital system and develop a machine learned assessment mechanism by which a wheezing pattern is recognized based on a learned threshold rather than a preset threshold.

For example, one exemplary algorithm deployed to track data samples and determine wheezing thresholds may be support vector machine learning technique, which may be a supervised learning model with associated learning algorithm that analyze data used for classification and regression analysis. Accordingly a set of training examples may be given each marked as belonging to one or the other of categories and an SVM training algorithm builds a model that assigns new examples to one of the categories, making it a non-probabilistic binary and linear classifier. Such SVM model may be a representation of examples such as points in space, mapped so that the examples of the separate categories are divided by clear gap that is as wide as possible. Besides supervised learning, an unsupervised learning approach may be deployed, which attempts to find natural clustering of data groups, and then map new data to these formed clustered groups. The clustering algorithm provides an improvement to the support vector machine. Other techniques such as: decision trees, ordinary least squares regression, logistic regression, ensemble methods, clustering algorithms, principle component analysis, singular value decomposition, or independent component analysis could also be used individually or in some combination.

In the analysis part of the present disclosure, a wheezing condition may be detected, or a wheezing condition may not be detected. If not detected, mobile device 1018 may output a message or a signal or highlight indication of a no wheezing sign. This indicates that no wheezing has been detected at the particular location from which lung data has been processed.

If wheezing is detected, a classification may further determine the type of wheezing that is detected. For example, the detected wheezing may be inspiratory wheezing 1020. This is a wheezing detected a patient is inhaling and may be detected at a predetermined portion of the breathing cycle. For example, a breathing cycle may include an inhale portion and an exhale portion. Accordingly, depending on where a peak signal is detected, an inspiratory wheezing may be detected. Similarly, mobile device 600 may detect an expiratory wheezing at the location from which lung data is being received. As with inspiratory wheezing, mobile device 600 may detect the expiratory wheezing based on where a peak is detected within the breathing cycle.

If inspiratory and expiratory wheezing is detected in a single breathing cycle, then this type of wheezing may be classified as a biphasic wheezing 1024. If a signal is detected, however, the detected pattern does not fit the previous classifications, then a severe obstruction 1026 is determined. A severe obstruction 1026 may also include particular frequency signature that is unique to a severe obstruction classification. This signature pattern may be detected and saved as a severe obstruction condition in memory 650 during a preprocessing phase. For example, in severely obstructed airways no noise is detected, as such, there may not be anything to hear and that signature may be stored. Alternatively, when recording is initiated indicating that a signal is received, and nothing is heard, a severely obstructed airway condition may be classified.

When mobile device 600 classifies the wheezing condition, mobile device 600 outputs 1028 the classification on touch panel 630 and performs an additional operation before ending the processing/classification phase 1030. The additional operation, as will be further discussed herein, may include determining an asthma score, providing medical guidance and support, either based on the wheezing condition or the asthma score, contacting the doctor or the like.

FIG. 11 illustrates, according to one embodiment, a flowchart depicting the steps performed to process a lung signal and perform a support vector machine (SVM) classification. When a lung signal is received 1102 at mobile device 600, the device may be configured to perform a plurality of signal processing techniques aimed at conditioning and extracting features from the signals that equate to a classification of wheezing as described herein. Such signal processing may include performing adaptive thresholding 1104, performing peak selection 1110 and sound grouping, and performing feature extraction 1116.

Adaptive thresholding 1104 may include segmenting 1106 frequency of the lung signal into different frequency bands and defining a threshold value 1108 for each band and for each time point detected. For example, band-pass filtering may be performed in the 50-2000 Hz range, which is determined to be the frequency range of most lung sounds. This may be followed by normalization of the intensity (not shown).

The normalization process enables signal uniformity in the processing phase and includes setting the amplitudes of the lung signal within a specific range (e.g. ±1 range). The amplitude range of the lung signal may vary based on a plurality of factors, including recording conditions, location of the stethoscope on the chest, age, and sex of the patient. As such, the normalization process compensates for any patient-to-patient amplitude variations in the lung signal.

Another technique deployed before the adaptive thresholding is the use of the short-time Fourier Transform (STFT) which may be set at 40-ms time windows and a 50% window overlap rate. There are approximately 15 breathing cycles per minute in a typical breathing cycle, so a typical breathing cycle may be 4 second long.

Adaptive thresholding 1106 may be applied by segmenting the frequency axis into four frequency bands: 100-300 Hz, 300-500 Hz, 500-800 Hz, and 800-1000 Hz. For each band and for each time point, a threshold value may be defined as:

$$\text{Threshold} = \text{mean} + W^* \text{STD}$$

Where W=0.3, 0.3, 0.2 and 0.2 for the four frequency bands going from the lowest frequency band to the highest. Weights may be empirically set, based on trained data set with documented wheezing.

Peak selection and sound grouping 1110 includes identifying dominant signal peaks 1112 and grouping the dominant signal peaks along the time axis 1114. Identifying the dominant peaks includes identifying dominant signal peaks (local maxima) along the Y axis, if present and then grouping the dominant signal peaks along time points X-axis to identify sounds that last longer than a preset duration. The preset duration would be a certain percentage of the breathing cycle. For example, inspiratory or expiratory wheezes cannot be longer than half the breathing cycle. An alternative number may be selected, such as a fraction of a breathing cycle.

Once peaks are selected and grouped, feature extraction 1116 may be performed. Dominant 1118 and non-dominant 1120 features may be extracted. Dominant features are sound features that include time duration, mean frequency, mean intensity mean spectral width, and standard deviation of spectral width with threshold (20% of peak intensity). Non-dominant features are sound features that include standard deviation of mean frequencies, standard deviation of mean intensities, mean of mean intensities and number of sounds.

As described above, once features are extracted, SVM classification may be deployed to determine the classification of the lung signal into wheezing or non-wheezing. For example, features of the present disclosure may extract discriminative acoustic features of wheezing in time and frequency domains on the acquired lung recordings. The extracted features, together with pulse oximetry data, may form an input to machine learning-based classifiers. As a quality measure, the auscultated recordings are reviewed concordance in classification of the lung sounds as clear, inspiratory wheezing, expiratory wheezing, biphasic wheezing or diminished breath sounds. The output of the algorithm will be confirmed against the classification provided by the physician review.

The characterization and identification of lung sounds involves three stages: (1) preprocessing segments of the individual breathing cycles to determine the Respiratory Rate (RR); (2) representative feature extraction on breathing cycles and (3) classification of lung sounds based on machine learning.

In order to segment individual breathing cycles automatically and estimate the resting respiratory rate (RRR), we will use the modified Pan-Tompkin's peak detection method.

First a finite impulse response (FIR) band pass filter having a passband of 50 Hz-2000 Hz may be applied. This frequency range corresponds to the band in which the majority of lung sound information has been observed to occur. A point-wise absolute magnitude of the filtered signal may then be calculated. The resulting signal will then be normalized by subtracting the mean value. The derivative of the signal will be computed next to extract the slope information. This signal will be squared, to accentuate the peaks further. The signal is then integrated using a moving window. A judicious selection of the window width is necessary because if an integration window is too short, it could cause a single peak in the respiration signal to trigger false peaks with the detector. While, if the integration window is too long, it could miss peaks. The optimal window width will be 40 ms. Signal peaks may then be identified as associated with large energy bursts in the integrated waveform using an empirical threshold parameter. Detected peaks will identify the individual breathing cycles, the mean duration of which will be used to compute respiratory rate.

As described earlier, STFT may be used to compute the frequency characteristics of the recorded sound signal that determine the time dependence of the signal in the frequency domain.

Figure 13A:
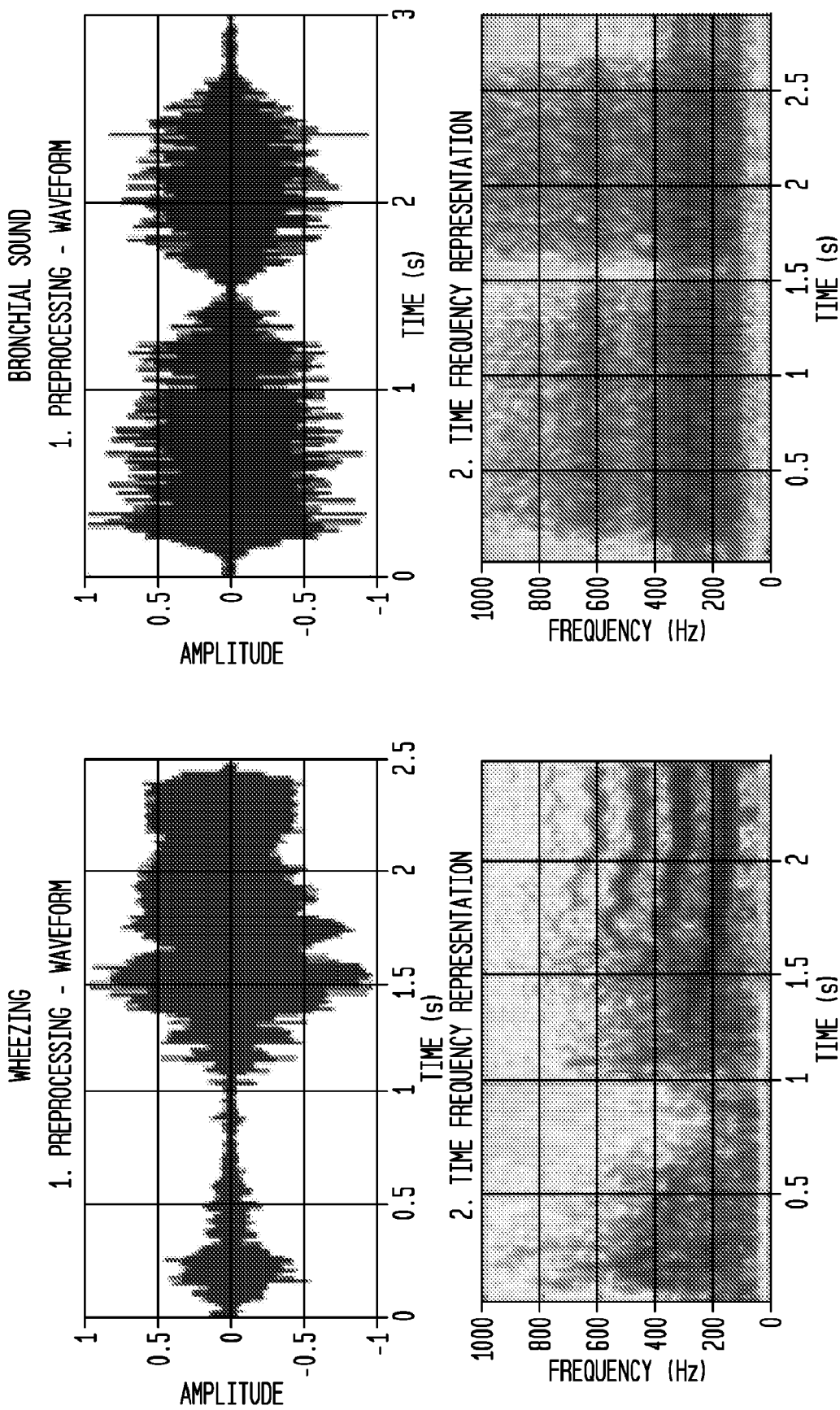
FIGS. 13A, 13B and 13C depict, according to one embodiment, signal processing of the lung signal based on short-time Fourier Transform (STFT) to compute the frequency characteristics and output a wheezing detection signal plot.

When a wheezing episode occurs, each STFT spectrum exhibits continual harmonic components along the time axis, such that the spectra are highly similar to each other as is further illustrated in FIG. 13A. STFT is computed for each segmented breathing cycle of sound signal over 40 ms windows with 50% overlap. FIG. 13A also shows the spectral variations by STFT in wheezing and bronchial (non-wheezing) patterns.

After adaptive thresholding in different frequency bands, same features are calculated, such as time duration, mean frequency, mean intensity, and mean and standard deviation of spectral width. The whole set of extracted features may be referred to as a bag of words (BoW). A BoW will comprise a concatenated vector of extracted features, pulse oximeter measurement, and RR. BoW may further include other inputs relating to Dyspnea and retraction.

In the SVM classification, the SVM classifier may be extended to multi-class classification incorporating new features like RR and pulse oximeter data. In the training process, there may be eight lung sound recordings from eight different sites on the chest as described earlier. Accordingly, each of the recordings may be labeled to be one from the category of clear, inspiratory wheezing, expiratory wheezing, biphasic wheezing or diminished breath sounds. Such a problem can be solved by a multi-categorical supervised classification technique in machine learning based on quantitative features of the lung sounds. In a supervised classification problem, representative features from training examples are extracted. Based on extracted features, the classifier is trained to distinguish among various classes. Once such a model is learned, at test time, a new test data is presented, and then model yields the corresponding label for that data.

It must be appreciated that additional and/or alternative site selection techniques and configurations as described above are well within the scope of the present disclosure. For instance, 11 different sites on the chest may be assigned based on desired accuracy and overall assessment of the wheezing condition. It may further be appreciated that other numbers of site selections may be configured and displayed.

Consequently, such a classification algorithm will establish a benchmark for the identification of wheezing phases.

Turning now to FIG. 12, the figure illustrates, according to one embodiment, a flowchart depicting the steps performed to process a lung signal and providing additional medical support after classification is performed, depicting the additional operation 1202. The additional operation may include saving the recording and associating with a patient file 1204, transmitting recording to a remote server 1206, and displaying detected condition 1208. If the detected condition is not wheezing, the process may end at step 1112. Alternatively, if the detected condition is wheezing, a determination of whether to issue a warning 1214 and based on a severity of detected wheezing. The warning may be a warning message 1216, a physician alert message 1218, alerting a designated person 1220, provide remedial measures and directions 1222, and locating the nearest ER facility 1226.

Warning message 1216 may be a message alerting the patient or care taker that a wheezing condition is serious and medical assistance may be required soon. Physician alert 1218 may include a message sent to a physician indicating a time, location and a synopsis of the recoded wheezing condition along with the classification. In this regard, a physician may be able to immediately perform a remote diagnosis based on objective testing results and provide immediate remedial measures and treatment.

Alerting a designated person 1220 may include transmitting a message to a designated person of interest. For example, the mobile device 600 may have therein stored a contact list including a mother, father or guardian of a child patient, or a spouse of an adult patient and the like. After detecting the wheezing condition, mobile device 600 may be configured to search for a designated person, either a person that has been preselected as a designated person, or a naming methodology, such as "mom" or "dad" or "husband" and the like may be relied on to determine the person. When such a designated person is detected, a message may be generated to alert the designated person of the findings. Such message may include a plurality of information, including, for example, time and location of the detection along with the diagnosis and severity of the diagnosis.

A remedial measure may also be output 1122 by mobile device 600. The remedial measure may include performing a technique to alleviate discomfort (e.g., steam treatment or the like) and may further include direction to take a medication of some sort. For example, if wheezing is detected at a plurality of locations, then an instruction may be issued alerting the patient of an impending asthma attack and recommend using an inhaler. If on the other hand the detected condition is one in which breathing is constricted, then an automatic emergency call may be triggered or a call may be set up awaiting confirmation by the patient or caretaker. In addition to or in the alternative, mobile device 600 may search for a location of a nearest ER facility and direct the patient to go to the ER facility. Such output may include navigation directions, hours of operation of the ER facility and the like. Additionally, mobile device 600 may determine whether a syncing operation may be performed in which the ER facility can receive the performed testing results prior to the patient checking in.

Figure 13B:
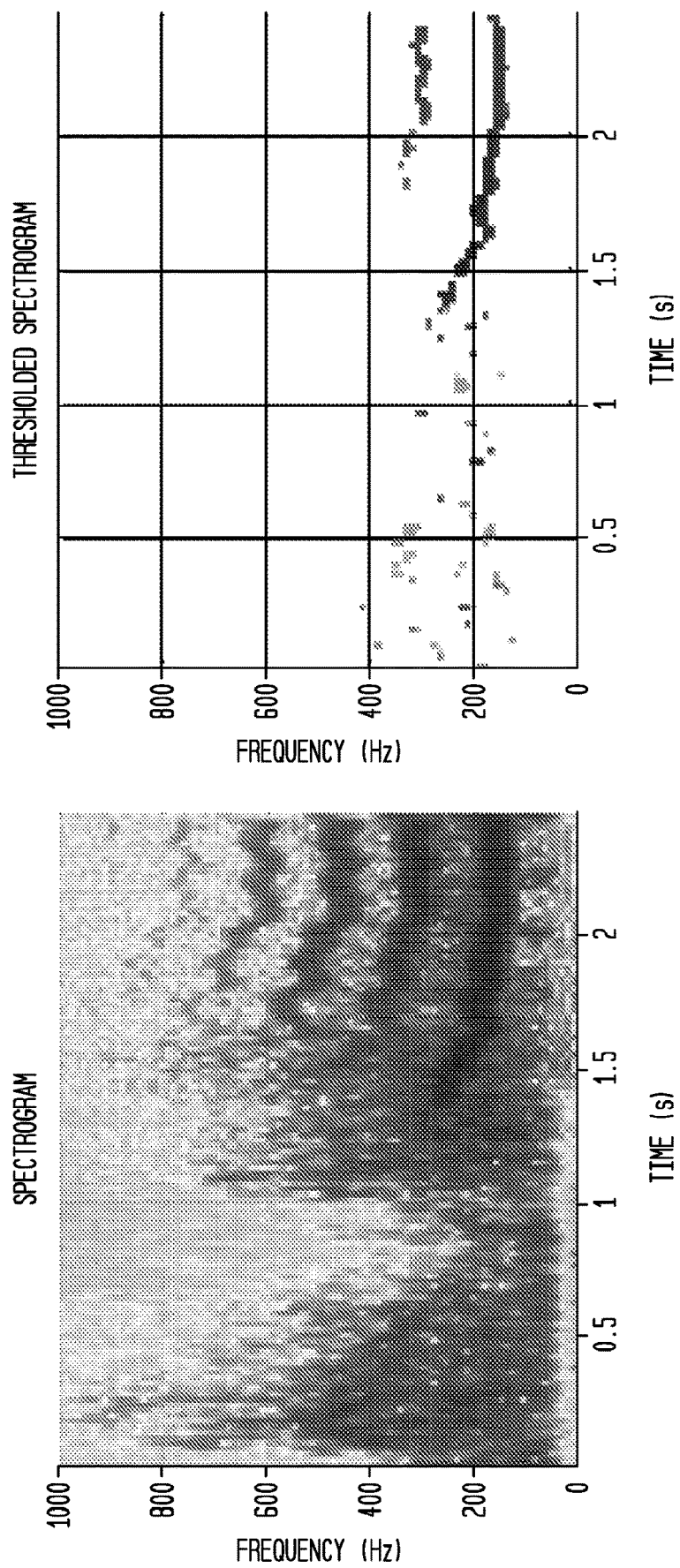
Figure 13C:
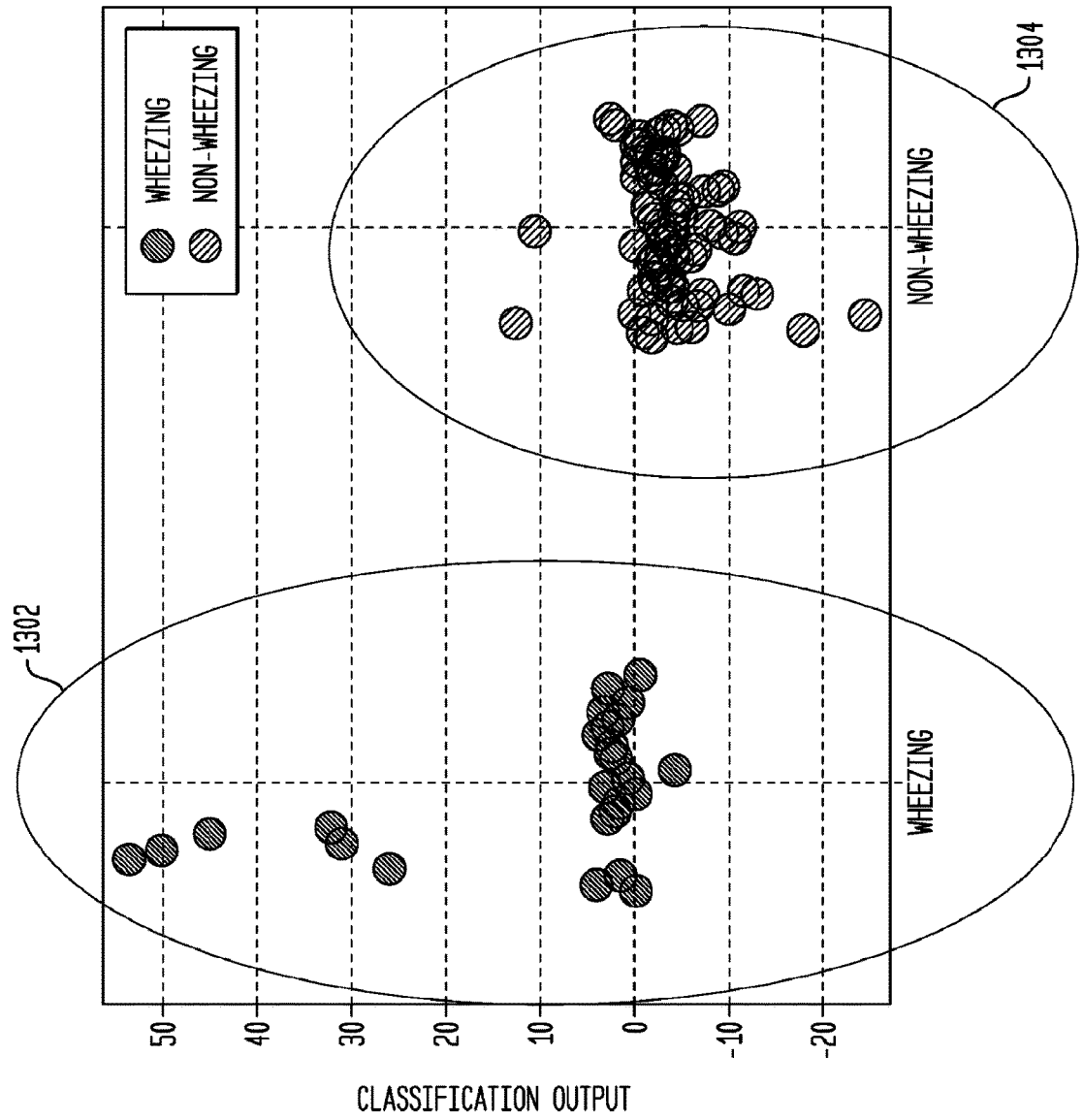

FIGS. 13A, 13B and 13C depict, according to one embodiment, signal processing of the lung signal based on short-time Fourier Transform (STFT) to compute the frequency characteristics and output a wheezing detection signal plot. In FIG. 13A, for example, when a wheezing episode occurs, each STFT spectrum exhibits continual harmonic components along the time axis, such that the spectra are highly similar to each other. STFT may be computed for each segmented breathing cycle of sound signal over 40 ms windows with 50% overlap. FIG. 13A also shows the spectral variations by STFT in wheezing and bronchial (non-wheezing) patterns. Accordingly, mobile device 600 can be configured to differentiate between a bronchial sound, a pneumonia sound and a wheezing sound.

FIG. 13B depicts a spectrogram of wheezing on the left and spectrogram with adaptive thresholding methodology on the right. The figure appears to be before adaptive thresholding. Wheeze frequency generally have harmonics, and that's why the frequency scale is divided into bands. In this regard, fundamental wheeze frequency can be determined as well as its harmonics. Harmonics are generally weaker so deferent criteria needs to be used in different bands.

FIG. 13C depicts the classification performed by the current signal processing algorithm, in which there is a clear distinction between wheezing detection and non-wheezing detection. Y axis units are in Hz.

Figure 14:
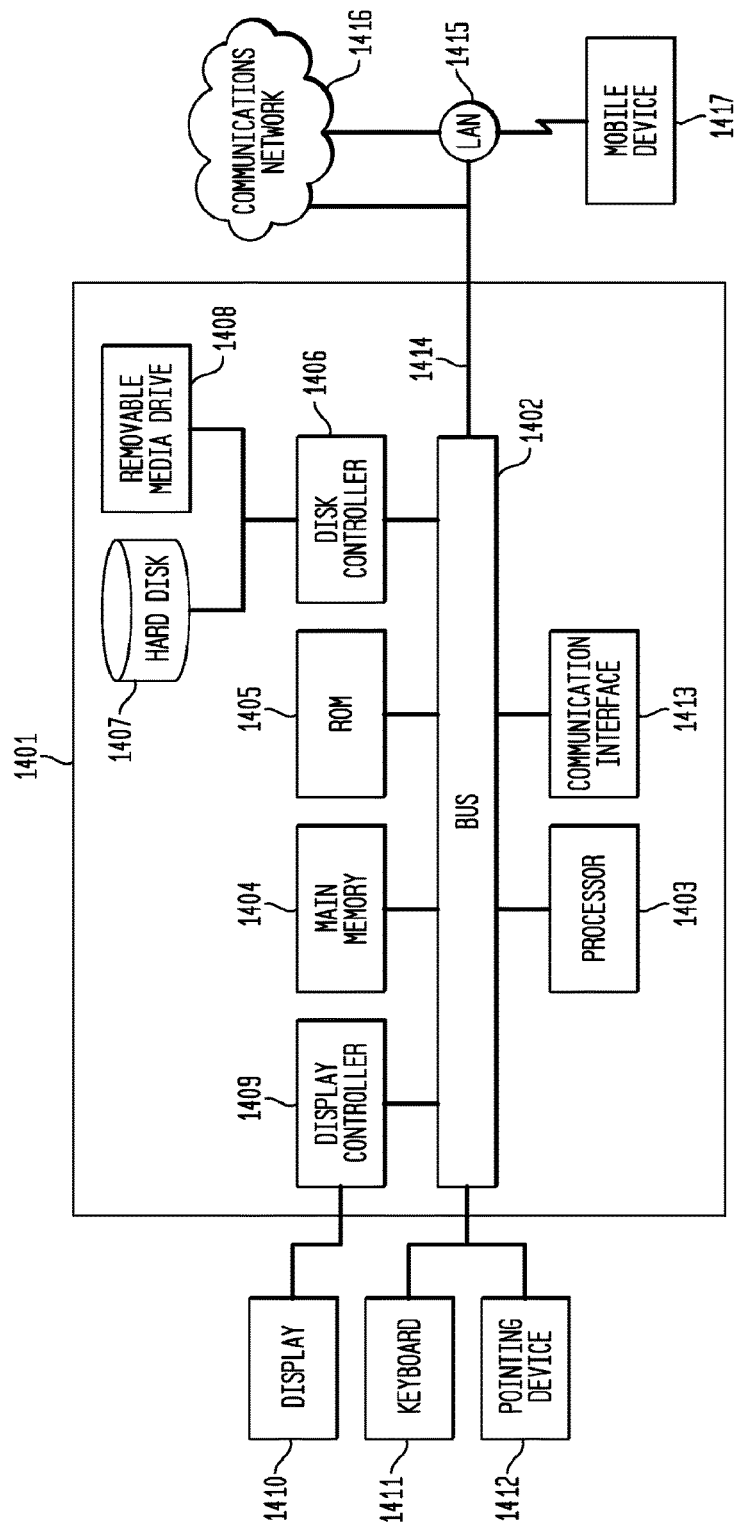
FIG. 14 illustrates a block diagram of a computing device according to one embodiment.

FIG. 14 illustrates a block diagram of a computing device according to one embodiment. Each of the functions of the described embodiments may be implemented by one or more processing circuits. A processing circuit or circuitry includes a programmed processor (for example, processor 1403 in FIG. 14), as a processor includes circuitry. A processing circuit also includes devices such as an application-specific integrated circuit (ASIC) and conventional circuit components arranged to perform the recited functions.

The various features discussed above may be implemented by a computer system (or programmable logic). FIG. 14 illustrates such a computer system 1401. Further, the computer system 1401 of FIG. 14 may be a special-purpose machine. In one embodiment, the computer system 1401 is a particular, special-purpose machine when the processor 1403 is programmed to process and analyze lung sounds in order to determine the presence of wheezing.

The computer system 1401 includes a disk controller 1406 coupled to the bus 1402 to control one or more non-transitory storage devices for storing information and instructions, such as a magnetic hard disk 1407, and a removable media drive 1408 (e.g., floppy disk drive, read-only compact disc drive, read/write compact disc drive, compact disc jukebox, tape drive, and removable magneto-optical drive). The storage devices may be added to the computer system 1401 using an appropriate device interface (e.g., small computer system interface (SCSI), integrated device electronics (IDE), enhanced-IDE (E-IDE), direct memory access (DMA), or ultra-DMA).

The computer system 1401 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1401 may also include a display controller 1409 coupled to the bus 1402 to control a display 1410, for displaying information to a computer user. The computer system includes input devices, such as a keyboard 1411 and a pointing device 1412, for interacting with a computer user and providing information to the processor 1403. The pointing device 1412, for example, may be a mouse, a trackball, a finger for a touch screen sensor, or a pointing stick for communicating direction information and command selections to the processor 1403 and for controlling cursor movement on the display 1410.

The processor 1403 executes one or more sequences of one or more instructions contained in a memory, such as the main memory 1404. Such instructions may be read into the main memory 1404 from another computer readable medium, such as a hard disk 1407 or a removable media drive 1408. One or more processors in a multi-processing arrangement may also be employed to execute the sequences of instructions contained in main memory 1404. In alternative embodiments, hard-wired circuitry may be used in place of or in combination with software instructions. Thus, embodiments are not limited to any specific combination of hardware circuitry and software.

As stated above, the computer system 1401 includes at least one computer readable medium or memory for holding instructions programmed according to any of the teachings of the present disclosure and for containing data structures, tables, records, or other data described herein. Examples of non-transitory computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium.

Stored on any one or on a combination of computer readable media, the present disclosure includes software for controlling the computer system 1401, for driving a device or devices for implementing the features of the present disclosure, and for enabling the computer system 1401 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1403 for execution. A computer readable medium may take many forms, including but not limited to, non-volatile media or volatile media. Non-volatile media includes, for example, optical, magnetic disks, and magneto-optical disks, such as the hard disk 1407 or the removable media drive 1408. Volatile media includes dynamic memory, such as the main memory 1404. Transmission media, on the contrary, includes coaxial cables, copper wire and fiber optics, including the wires that make up the bus 1402. Transmission media also may also take the form of acoustic or light waves, such as those generated during radio wave and infrared data communications.

Various forms of computer readable media may be involved in carrying out one or more sequences of one or more instructions to processor 1403 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1401 may receive the data on the telephone line and place the data on the bus 1402. The bus 1402 carries the data to the main memory 1404, from which the processor 1403 retrieves and executes the instructions. The instructions received by the main memory 1404 may optionally be stored on storage device 1407 or 1408 either before or after execution by processor 1403.

The computer system 1401 also includes a communication interface 1413 coupled to the bus 1402. The communication interface 1413 provides a two-way data communication coupling to a network link 1414 that is connected to, for example, a local area network (LAN) 1415, or to another communications network 1416 such as the Internet. For example, the communication interface 1413 may be a network interface card to attach to any packet switched LAN. As another example, the communication interface 1413 may be an integrated services digital network (ISDN) card. Wireless links may also be implemented. In any such implementation, the communication interface 1413 sends and receives electrical, electromagnetic or optical signals that carry digital data streams representing various types of information.

The network link 1414 typically provides data communication through one or more networks to other data devices. For example, the network link 1414 may provide a connection to another computer through a local network 1415 (e.g., a LAN) or through equipment operated by a service provider, which provides communication services through a communications network 1416. The local network 1414 and the communications network 1416 use, for example, electrical, electromagnetic, or optical signals that carry digital data streams, and the associated physical layer (e.g., CAT 5 cable, coaxial cable, optical fiber, etc.). The signals through the various networks and the signals on the network link 1414 and through the communication interface 1413, which carry the digital data to and from the computer system 1401 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1401 can transmit and receive data, including program code, through the network(s) 1415 and 1416, the network link 1414 and the communication interface 1413. Moreover, the network link 1414 may provide a connection through a LAN 1415 to a mobile device 1417 such as a personal digital assistant (PDA) laptop computer, or cellular telephone.

Figure 15:
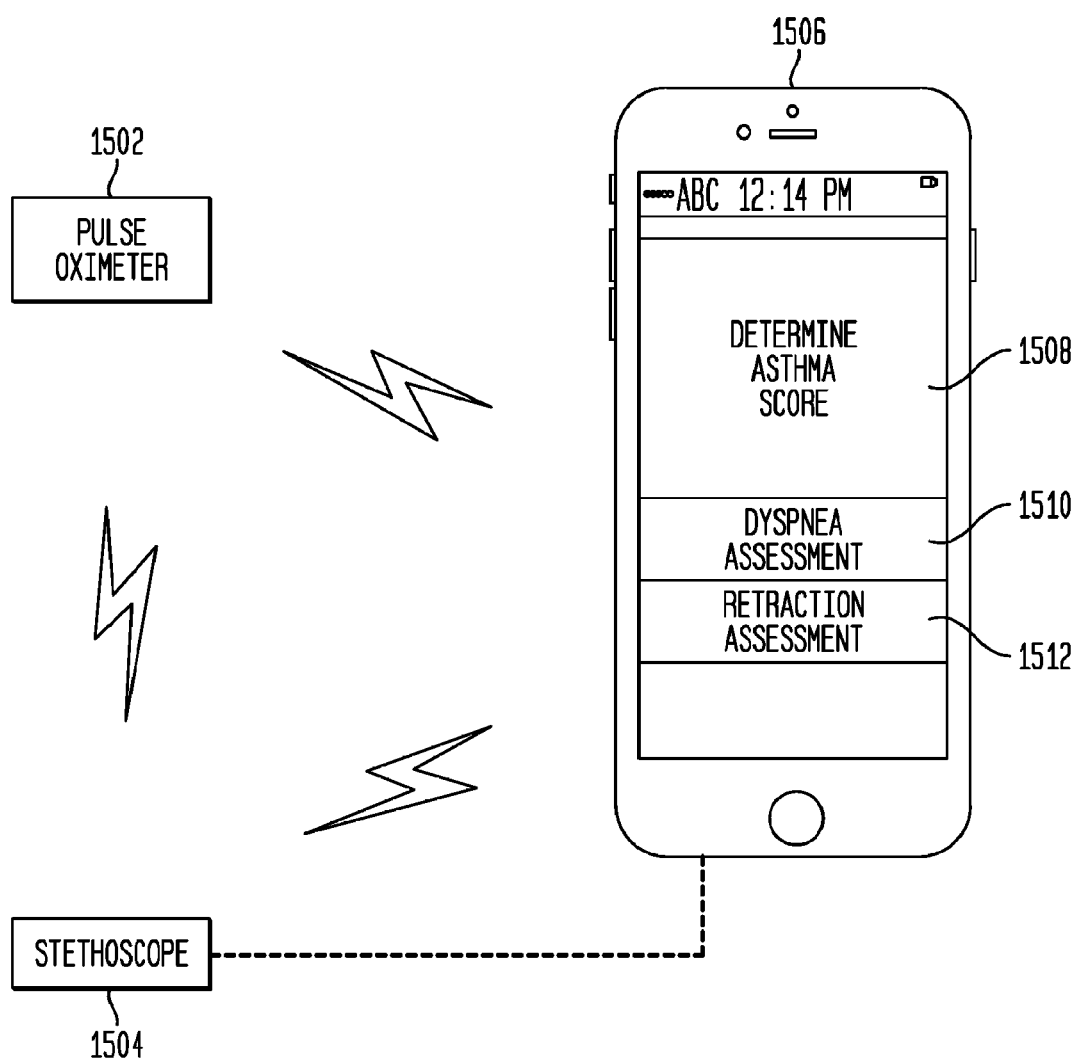
FIG. 15 illustrates an asthma score determination application based on pulse oximeter readings and other parameters.

FIG. 15 illustrates an asthma score determination application based on pulse oximeter readings and other parameters. As described herein, it is beneficial to perform a wheezing and asthma diagnosis on demand, at home or a pre-diagnosis before seeing a doctor. The benefits include continuous monitoring of chronic issues, reduced need to go to an ER every time a wheezing occurs, and provides the ability to diagnose, treat, and remedy a wheezing or asthma episode in the comfort of one's home, on the basis of continuous monitoring. This reduces costs for the patients, as a patient no longer needs to go to a doctor after or during each episode. This also provides objective measures that can be relied on by medical professionals in providing additional remedial measures. Additionally, the present disclosure also allows for the monitoring, documenting, and tracking of each asthma and wheezing episode, and for a plurality of times and locations. Such a device provides improvements, not only in the health care provided, and the expediency by which such health care is provided, but also provides a unique way in which a technical device can perform detection of wheezing remotely and provide a patient with real life medical solutions on demand.

Such technical improvements may be further strengthened using the embodiment described in FIGS. 15 and 16. In this embodiment, besides determining wheezing, a further determination of an asthma score may be carried out. An asthma score may provide yet a more complete picture and analysis of the asthmatic condition of a patient remotely. To this end, FIG. 15, for example, describes yet another embodiment in which a detection system 1500 includes a pulse oximeter 1502 stethoscope 1504 and a mobile device 1506. These devices may communicate in a plurality of ways, as described herein the present disclosure. For simplification, an embodiment of the present disclosure utilizes wireless technologies, such as those described herein to communicate between the devices. For example, pulse oximeter 1502 may transmit the measured oxygen saturation levels to stethoscope 1504 or directly to mobile device 1506.

It must be appreciated that additional and/or alternative configurations of the detection system as described above are well within the scope of the present disclosure. For instance, the devices described herein may all be included within a single diagnostic device for ease of packaging and reduction in price. Accordingly, there may be envisioned a mobile device that is capable of detecting the lung signal and processing the lung signal, along with other detected features, as described further herein after. Such a device may reduce the need for attachments and peripheral devices, for example.

A patient may determine an asthma score before any wheezing detection is conducted or shortly thereafter. Upon selecting a request for determining an asthma score, or after computing a wheezing classification activity, mobile device 1506 may prompt a patient to determine the patient's asthma score 1508. In this case, it is envisioned that an asthma score takes a plurality of factors into consideration, including wheezing, oxygen saturation levels, resting respiratory rate, presence of dyspnea and retraction.

In one embodiment, an asthma score may rely solely on wheezing, oxygen saturation and measured resting respiratory rate. Conversely, other embodiments may include calculation of an asthma score including any one of the above combination including all of the above-noted features. For illustrative purposes, an example is described herein where an asthma score is calculated based on all five parameters listed herein.

FIG. 16 illustrates, according to an embodiment, a flow chart depicting the steps performed to determine the asthma score and providing health care/medical support based on the detected asthma score.

Process 1600 includes receiving a request 1602 for calculating an asthma score at the mobile device 1504. Accordingly mobile device 1504 may begin a data processing step 1604 that performs readings to measure all of the above-noted parameters. An order by which such parameters are measured is not particular and may be performed in any order available. Accordingly, data processing may include activate/receive and process 1606 oximeter data and determine 1608 oxygen saturation rate. Step 1604 includes processing stethoscope data 1610, as described herein, and provide a determination of a wheezing condition 1612 and a resting respiratory rate 1604. Once measured, it is worth noting that patients of different ages may have a different respiratory rate as a normal baseline. For example, a normal respiratory rate for a 1 year old patient may be much higher than a normal respiratory rate for a 20 year old patient. Measurement of respiratory rate may take up to one minute in order to provide an accurate reading. Other measurement times may also be applicable.

To measure a Dyspnea score, mobile device 1504 may activate a microphone 1616, provide a speaking excerpt or instructions 1618 and record the speech provided by the patient. Such detection here may include natural language detection to determine slurred speech and the like. Machine learning algorithms can be used in this instance as well to determine appropriate Dyspnea scores based on a training set for example which has Physician input which correlate to recorded values. Accordingly, at 1620 the mobile device determines a Dyspnea score.

A retraction rate may also be measured. Retractions may include sucking of the skin between or around the bones of the chest when inhaling. Retractions may also affect other body parts and may be associated with unique physical symptoms such as head bobbing and the like. When retractions occur, they illustrate a sign of increased use of the chest muscle for breathing. Accordingly, in one embodiment, a retraction rate may be determined by activating a camera within the mobile device, such as a camera within sensor section 608 described in FIG. 6. Mobile device 1504 may be configured to detect retractions within a predetermined period of time, such as 10 seconds, or the like to calculate a rate. Machine learning can also be used to determine the retraction score.

When the oxygen saturate rate, wheezing, resting respiratory rate, Dyspnea and retraction rates are calculated, mobile device may apply a weighting factor to each parameter in order to provide an overall asthma score. Once calculated, mobile device 1504 may output the asthma score on the touch panel and provide additional guidance. For example, if the score is below a threshold, then asthma may not be detected, or an asthma attack is not currently impending. Accordingly mobile device may record the findings to patient file 1632 and end the process. Alternatively, if the asthma score is above a threshold score, mobile device may issue a warning 1634 based on the score severity.

The warning may be a warning message 1636, a physician alert message 1638, alerting a designated person 1640, provide remedial measures and directions 1642, and/or locating the nearest ER facility 1644.

Warning message 1636 may be a message alerting the patient or care taker that a wheezing condition is serious and medical assistance may be required soon. Physician alert 1638 may include a message sent to a physician indicating a time, location and a synopsis of the recoded wheezing condition along with the classification. In this regard, a physician may be able to immediately perform a remote diagnosis based on objective testing results and provide immediate remedial measures and treatment.

Alerting a designated person 1640 may include transmitting a message to a designated person of interest. For example, the mobile device 1504 may have therein stored a contact list including a mother, father or guardian of a child patient, or a spouse of an adult patient and the like. After detecting the wheezing condition, mobile device 1504 may be configured to search for a designated person, either a person that has been preselected as a designated person, or a naming methodology, such as "morn" or "dad" or "husband" and the like may be relied on to determine the person. When such a designated person is detected, a message may be generated to alert the designated person of the findings. Such message may include a plurality of information, including, for example, time and location of the detection along with the diagnosis and severity of the diagnosis.

A remedial measure may also be output 1642 by mobile device 1504. The remedial measure may include performing a technique to alleviate discomfort (e.g., steam treatment or the like) and may further include direction to take a medication of some sort. For example, if wheezing is detected at a plurality of locations, then an instruction may be issued alerting the patient of an impending asthma attack and recommend using an inhaler. If on the other hand the detected condition is one in which breathing is constricted, then an automatic emergency call may be triggered or a call may be set up awaiting confirmation by the patient or caretaker. In addition to or in the alternative, mobile device 1504 may search for a location of a nearest ER facility 1644 and direct the patient to go to the ER facility. Such output may include navigation directions, hours of operation of the ER facility and the like. Additionally, mobile device 1504 may determine whether a syncing operation may be performed in which the ER facility can receive the performed testing results prior to the patient checking in. Alternatively, the device could be connected to a drug administration system that would administer a drug (such as steroids or an anti-inflammatory) in response to a particular score.

It must be appreciated that additional and/or alternative configurations of the warning/remedial measurements provided as described above are well within the scope of the present disclosure. For instance, in the case of a high asthma score being calculated, besides sending an alert message to the patient's physician 1638, a video conference request may be transmitted to the doctor well. This enables the doctor to view the results and then participate in a diagnostic video conference with the patient in order to determine the best course forward.

FIG. 17 illustrates, according to an embodiment, a chart depicting possible parameters and values used to determine the asthma score. A weighted factoring may be utilized as described above. In the alternative, a characteristic scoring may be utilized as described in FIG. 17. For example, a respiratory rate is provided a certain score depending on the measured parameters and the patient profile information. A patient who is 5 years old for example, with a RRR of 41 may receive a score of 2 or higher, but may receive a score of 1 if the measured RRR is between 31 and 35. In this example, the sampling period may be set at 30 seconds. Alternative embodiments may utilize different time factors of 60 seconds. Similarly, oxygen saturation rates receive different scores depending on the measured rate. A similar approach may be used for auscultation measurements, retractions (work of breathing) and Dyspnea.

As envisioned by the above-noted embodiments, the present disclosure aims to provide a real time solution to measuring, managing and treating asthma related symptoms including, wheezing detection and treatment. Such detection and treatment methodologies provide medical and technical improvements over existing methodologies in that parents or patients may be able to perform the measurements and diagnostics themselves without resorting to doctor or ER visits at every possible instance. This saves time and money. Additionally, the testing parameters and recordings are of the objective nature and thus, provide high accuracy measurements of asthma related parameters. Such detection devices can then provide real time analysis and diagnostics to a remote medical professional, and/or provide remedial solutions instantaneously. Such remedial solutions are in line with health professional approved methodologies.

As can be appreciated, the chronic nature of the asthma condition requires constant monitoring and treatment for patients. Accordingly, the embodiments of the present disclosure provide a device, system and methodology that enables simple, real time, in home detection of wheezing and other asthma related parameters, communication with a doctor, tracking of the diagnostics, and real time remedial measures.

Turning now to FIG. 18, the figure illustrates, according to an embodiment, a flow chart 1800 depicting the steps performed to determine the asthmatic condition based on received parameters. FIG. 18 describes that the mobile device receives a lung signal 1802, after which the device circuitry may, in response to receiving an activation command, display 1804 a patient recording canvas corresponding to physical locations on a body of the patient, the canvas including an anterior patient orientation and a posterior patient orientation. Furthermore, in response to receiving an indication of a detected lung signal, the circuitry may also generate 1806 a recording process, the recording process including recording, for a predetermined period of time, the detected lung signal, and associating the recording with a marked location, from among a plurality of marked locations within the patient recording canvas, and indicate 1808 a new marked location for recording until each marked location is associated with a recording. Thereafter, the circuitry may merge 1810 the recorded lung signal from each marked location on the patient recording canvas as merged information, and apply 1812 processing to the merged information to generate the asthmatic condition indication.

While aspects of the present disclosure have been described in conjunction with the specific embodiments thereof that are proposed as examples, alternatives, modifications, and variations to the examples may be made. Furthermore, the above disclosure also encompasses the embodiments noted below. It should be noted that, as used in the specification and the appended claims, the singular forms "a," "an," and "the" include plural referents unless the context clearly dictates otherwise.

The invention claimed is:

1. A computer enhanced medical device for generating an indication for an asthmatic condition, comprising:
an input port configured to receive a lung signal from a stethoscope, the lung signal having been converted from an analog signal to a digital signal; and
circuitry configured to
in response to receiving an activation command, display a patient recording image corresponding to physical locations on a body of a patient, the image including an anterior patient orientation and a posterior patient orientation,
detect the lung signal,
in response to detecting the lung signal, initiate a recording process, the recording process including recording, for a predetermined period of time, the lung signal, and associating a recording of the lung signal with a marked location, from among a plurality of marked locations within the patient recording image,
repeat an indication of a new marked location from the plurality of marked locations and an initiation of the recording process for the new marked location until each of the plurality of marked locations is associated with a recorded lung signal,
merge the recorded lung signal from each of the plurality of marked locations on the patient recording image as merged information, and
apply machine learning processing to the merged information to generate the indication for the asthmatic condition, the indication signifying a reason for medical attention,
wherein applying the machine learning processing to generate the indication includes detecting a pattern in the merged information and using pattern recognition to identify the asthmatic condition based on a learned threshold in real time.

2. The device according to claim 1, wherein the circuitry is further configured to store the merged information in a patient file.

3. The device according to claim 2, wherein if the lung signal is not detected, the circuitry is further configured to
indicate the marked location on the patient recording image for a user to generate the lung signal from,
detect a user selection of the marked location on the patient recording image, and
initiate the recording process for a predetermined period of time.

4. The device according to claim 3, wherein the circuitry is further configured to indicate a new location on the patient recording image from which to generate the lung signal if the user selection of the marked location on the patient recording image is not detected.

5. The device according to claim 2, wherein in analyzing the merged information, the circuitry is further configured to perform a signal pre-processing including
performing a filtering operation on the recorded lung signal, the filtering operation including using a band pass filter configured to filter in a range between 50 Hz and 2000 Hz, and
performing a short-time Fourier Transform on the filtered signal, the transform including a 40 ms time window and a window overlap rate of 50%.

6. The device according to claim 5, wherein the circuitry is further configured to perform adaptive thresholding in different frequency bands by segmenting a frequency axis into four different frequency bands and calculating a threshold value for each frequency band, wherein the threshold is calculated as: Threshold=mean+w*STD, mean being the mean being the average value of data points within the frequency band, w being a weighted factor and STD being a standard deviation value for the data points within the frequency band.

7. The device according to claim 2, wherein the circuitry is further configured to detect a wheezing condition as being at least one of clear breath sounds (no wheezing), inspiratory wheezing, expiratory wheezing, biphasic wheezing, and severely obstructed airway.

8. The device according to claim 7, wherein upon determining the wheezing condition, the circuitry is further configured to
transmit the merged information to a remote server, and
output a remedial solution based on the wheezing condition.

9. The device according to claim 8, wherein the circuitry is further configured to, in response to the wheezing condition being a severely obstructed airway, locate a nearest emergency medical facility and output directions to the emergency medical facility.

10. The device according to claim 8, wherein the circuitry is further configured to
in response to the wheezing condition being an inspiratory, expiratory or biphasic wheezing condition,
transmit an alert message to an electronic device associated with a medical provider, the alert message including the merged information, and
transmit a second alert message to an electronic device associated with a guardian or caretaker of the patient.

11. The device according to claim 2, wherein the circuitry is further configured to
receive an oximeter signal including oxygen saturation levels, and
generate the indication for the asthmatic condition by
determining a resting respiratory rate based on the merged information,
determining a Dyspnea score of the patient by
activating a microphone within the device,
outputting speaking instructions for the patient to speak,
detecting a natural language speech pattern, and
outputting a Dyspnea score,
determining a retraction rate by
activating a camera within the device,
measuring physical symptoms, including chest retractions, and
based on severity of the chest retractions, outputting a retraction score, and
determining and outputting an asthma score by applying weighting factors to the oxygen saturation levels, the resting respiratory rate, the retraction rate and the Dyspnea score,
wherein the indication for the asthmatic condition is based on the asthma score.

12. The device according to claim 11, wherein the circuitry is further configured to
in response to the asthma score being below a severity threshold, save the merged information to the patient file and transmit a file update to the a remote server, and
in response to the asthma score being above the severity threshold, display a warning and transmit at least one alert message to a physician associated with the patient.

13. A computer enhanced medical method for generating an indication for an asthmatic condition, comprising:
receiving, at an input port of a mobile device, a lung signal from a stethoscope, the lung signal having been converted from an analog signal to a digital signal;
in response to receiving an activation command, displaying a patient recording image corresponding to physical locations on a body of a the patient, the image including an anterior patient orientation and a posterior patient orientation;
detecting the lung signal;
in response to detecting the lung signal, initiating a recording process, the recording process including recording, for a predetermined period of time, the lung signal, and associating a recording of the lung signal with a marked location, from among a plurality of marked locations within the patient recording image;
repeating an indication of a new marked location from the plurality of marked locations and an initiation of the recording process for the new marked location until each of the plurality of marked locations is associated with a recorded lung signal;
merging the recorded lung signal from each of the plurality of marked locations on the patent recording image as merged information; and
applying machine learning processing to the merged information to generate the indication for the asthmatic condition, the indication signifying a reason for medical attention,
wherein applying the machine learning processing to generate the indication includes detecting a pattern in the merged information and using pattern recognition to identify the asthmatic condition based on a learned threshold in real time.

14. The method according to claim 13, further comprising:
if the lung signal is not detected,
indicating the marked location on the patient recording image for a user to generate a the lung signal from,
detecting a user selection of the marked location on the patient recording image, and
triggering the recording process for the predetermined period of time.

15. The method according to claim 14 further comprising indicating a new location on the patient recording image from which to generate the lung signal if the user selection is not detected.

16. The method according to claim 13, further comprising:
receiving an oximeter signal including oxygen saturation levels; and
generating the indication for the asthmatic condition by
determining a resting respiratory rate based on the merged information;
determining a Dyspnea score of the patient by
activating a microphone within a mobile device,
outputting speaking instructions for the patient to speak,
detecting a natural language speech pattern, and
outputting the Dyspnea score;
determining a retraction rate by
activating a camera within the mobile device,
measuring physical symptoms, including chest retractions, and
based on severity of the chest retractions, outputting a retraction score; and determining and outputting an asthma score by applying weighting factors to the oxygen saturation levels, the resting respiratory rate, the retraction rate and the Dyspnea score,
wherein the indication for the asthmatic condition is based on the asthma score.

17. The method according to claim 16, further comprising:
in response to the asthma score being below a severity threshold, saving the merged information to a patient file and transmitting a file update to a remote server; and
in response to the asthma score being above the severity threshold, displaying a warning and transmitting at least one alert message to a physician associated with the patient.

18. A non-transitory computer readable medium having stored thereon a program that when executed by a computer causes the computer to implement a computer enhanced medical method for generating an indication for an asthmatic condition, comprising:
receiving, at an input port of a mobile device, a lung signal from a stethoscope, the lung signal having been converted from an analog signal to a digital signal;
in response to receiving an activation command, displaying a patient recording image corresponding to physical locations on a body of a patient, the image including an anterior patient orientation and a posterior patient orientation;
detecting the lung signal,
in response to detecting the lung signal, initiating a recording process, the recording process including recording, for a predetermined period of time, the lung signal, and associating a recording of the lung signal with a marked location, from among a plurality of marked locations within the patient recording image;
repeating an indication of a new marked location from the plurality of marked locations and an initiation of the recording process for the new marked location until each of the plurality of marked locations is associated with a recorded lung signal;
merging the recorded lung signal from each of the plurality of marked locations on the patent recording image as merged information; and
applying machine learning processing to the merged information to generate the indication for the asthmatic condition, the indication signifying a reason for medical attention,
wherein applying the machine learning processing to generate the indication includes detecting a pattern in the merged information and using pattern recognition to identify the asthmatic condition based on a learned threshold in real time.

19. The non-transitory computer readable medium according to claim 18, further comprising detecting a wheezing condition as being at least one of clear breath sounds (no wheezing), inspiratory wheezing, expiratory wheezing, biphasic wheezing and severely obstructed airway.

20. The non-transitory computer readable medium according to claim 18, further comprising:

receiving an oximeter signal including oxygen saturation levels; and
generating the indication for the asthmatic condition by determining a resting respiratory rate based on the merged information;
determining a Dyspnea score of the patient by
  activating a microphone within a mobile device,
  outputting speaking instructions for the patient to speak,
  detecting a natural language speech pattern, and
  outputting the Dyspnea score;
determining a retraction rate by
  activating a camera within the mobile device,
  measuring physical symptoms, including chest retractions, and based on
severity of the chest retractions,
  outputting a retraction score; and
determining and outputting an asthma score by applying weighting factors to the oxygen saturation levels, the resting respiratory rate, the retraction rate and the Dyspnea score,
wherein the indication for the asthmatic condition is based on the asthma score.

\* \* \* \* \*